United States Patent
Nohr et al.

(10) Patent No.: US 6,277,897 B1
(45) Date of Patent: Aug. 21, 2001

(54) PHOTOINITIATORS AND APPLICATIONS THEREFOR

(75) Inventors: Ronald Sinclair Nohr, Alpharetta; John Gavin MacDonald, Decatur, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/325,516

(22) Filed: Jun. 3, 1999

Related U.S. Application Data

(60) Provisional application No. 60/087,866, filed on Jun. 3, 1998.

(51) Int. Cl.[7] .......................... C07C 43/16; C07C 43/215; C08J 7/18; C08F 2/50
(52) U.S. Cl. .................. 522/34; 522/36; 522/39; 522/50; 522/55; 522/57; 522/63; 522/65; 522/75; 522/2; 523/160; 523/300; 430/270.1; 430/281.1; 568/583; 568/584; 427/511; 427/513; 427/514; 427/517; 427/520
(58) Field of Search .................. 522/50, 55, 57, 522/34, 36, 39, 63, 65, 75; 568/583, 584; 523/160, 300; 430/270.1, 281.1; 427/511, 513, 514, 517, 520

(56) References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,005,378 | 6/1935 | Kiel . |

(List continued on next page.)

FOREIGN PATENT DOCUMENTS

| | | |
|---|---|---|
| 103085 | 4/1937 | (AU) . |
| 12624/88 | 9/1988 | (AU) . |
| 620075 | 5/1962 | (BE) . |
| 637169 | 3/1964 | (BE) . |
| 413257 | 10/1932 | (CA) . |
| 458808 | 12/1936 | (CA) . |
| 460268 | 10/1949 | (CA) . |
| 461082 | 11/1949 | (CA) . |
| 463021 | 2/1950 | (CA) . |
| 463022 | 2/1950 | (CA) . |
| 465495 | 5/1950 | (CA) . |
| 465496 | 5/1950 | (CA) . |
| 465499 | 5/1950 | (CA) . |
| 483214 | 5/1952 | (CA) . |
| 517364 | 10/1955 | (CA) . |
| 537687 | 3/1957 | (CA) . |
| 552565 | 2/1958 | (CA) . |
| 571792 | 3/1959 | (CA) . |
| 779239 | 2/1968 | (CA) . |
| 930103 | 7/1973 | (CA) . |

(List continued on next page.)

OTHER PUBLICATIONS

R.T. Morrison & R.N. Boyd, "Organic Chemistry", pp. 174 and 707–711, Allen and Bacon, Boston,1959.*

Noguchi, H. UV Curable, Aqueous Ink Jet Ink: Material Design and Performance for Digital Printing 1998 International Conf. on Digital Printing Technologies 107–110 1998.

ESP@CENET databse JP 10324836 (Omron Corp.), Dec. 8, 1998. abstract 1998.

Derwent World Patents Index JP 8002092 (Mitsubishi Paper Mills Ltd.) Jan. 9, 1996. abstract.

Kubat et al. "Photophysical properties of metal complexes of meso–tetrakis (40sulphonatophenyl) porphyrin," *J. Photochem. and Photobiol.* 96 93–97 1996.

Derwent World Patents Index EP 659039 (Canon KK) Jun. 21, 1995. abstract.

Derwent World Patents Index JP 7061114 (Dainippon Printing Co. Ltd.) Mar. 7, 1995. abstract 1995.

Abstract for WO 95/00343—A1 *Textiles: Paper: Cellulose,* p. 7 1995.

Maki, Y. et al. "A novel heterocyclic N–oxide, pyrimido[5, 4–g]pteridinetetrone 5–oxide, with multifunctional photo-oxidative properties" *Chemical Abstracts* 122 925 [No. 122:31350 F] 1995.

Abstract of patent, JP 6–80915 (Canon, Inc.), Mar. 22, 1994.

Abstract of patent, JP 06–43573 (Iku Meji) (Feb. 18, 1994) 1994.

Pitchumani, K. et al. "Modification of chemical reactivity upon cyclodextrin encapsulation" *Chemical Abstracts* 121 982 [No. 121:13362 4v] 1994.

Wijesekera, T.P., et al. Synthetic Aspects of Pophyrin and Metalloporphyrin Chemistry *Metalloporpyrins in Catalytic Oxidations* pp. 202–203, 206–207, 1994.

(List continued on next page.)

*Primary Examiner*—Susan W. Berman
(74) *Attorney, Agent, or Firm*—Kilpatrick Stockton LLP

(57) ABSTRACT

The present invention is directed to new, energy-efficient photoinitiators in the form of α-amino enol ether compounds. The present invention is also directed to a method of generating reactive species, which includes exposing one or more photoinitiators to radiation to form one or more reactive species. Also described are methods of polymerizing unsaturated monomers, methods of curing an unsaturated oligomer/monomer mixture, and methods of laminating using the photoinitiators of the present invention.

19 Claims, No Drawings

U.S. PATENT DOCUMENTS

| | | |
|---|---|---|
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,320,080 | 5/1967 | Mazzarella et al. . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,488,269 | * 1/1970 | Allen et al. . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |

| | | |
|---|---|---|
| 3,689,565 | 9/1972 | Hoffmann et al. . |
| 3,694,241 | 9/1972 | Guthrie et al. . |
| 3,695,879 | 10/1972 | Laming et al. . |
| 3,697,280 | 10/1972 | Strilko . |
| 3,705,043 | 12/1972 | Zablak . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,801,329 | 4/1974 | Sandner et al. . |
| 3,817,752 | 6/1974 | Laridon et al. . |
| 3,840,338 | 10/1974 | Zviak et al. . |
| 3,844,790 | 10/1974 | Chang et al. . |
| 3,870,524 | 3/1975 | Watanabe et al. . |
| 3,873,500 | 3/1975 | Kato et al. . |
| 3,876,496 | 4/1975 | Lozano . |
| 3,887,450 | 6/1975 | Gilano et al. . |
| 3,895,949 | 7/1975 | Akamatsu . |
| 3,901,779 | 8/1975 | Mani . |
| 3,904,562 | 9/1975 | Hopfenberg et al. . |
| 3,910,993 | 10/1975 | Avar et al. . |
| 3,914,165 | 10/1975 | Gaske . |
| 3,914,166 | 10/1975 | Rudolph et al. . |
| 3,915,824 | 10/1975 | McGinniss . |
| 3,919,323 | 11/1975 | Houlihan et al. . |
| 3,926,641 | 12/1975 | Rosen . |
| 3,928,264 | 12/1975 | Young, Jr. et al. . |
| 3,933,682 | 1/1976 | Bean . |
| 3,952,129 | 4/1976 | Matsukawa et al. . |
| 3,960,685 | 6/1976 | Sano et al. . |
| 3,965,157 | 6/1976 | Harrison . |
| 3,978,132 | 8/1976 | Houlihan et al. . |
| 3,984,248 | 10/1976 | Sturmer . |
| 3,988,154 | 10/1976 | Sturmer . |
| 4,004,998 | 1/1977 | Rosen . |
| 4,012,256 | 3/1977 | Levinos . |
| 4,017,652 | 4/1977 | Gruber . |
| 4,022,674 | 5/1977 | Rosen . |
| 4,024,324 | 5/1977 | Sparks . |
| 4,039,332 | 8/1977 | Kokelenberg et al. . |
| 4,043,819 | 8/1977 | Baumann . |
| 4,048,034 | 9/1977 | Martan . |
| 4,054,719 | 10/1977 | Cordes, III . |
| 4,056,665 | 11/1977 | Tayler et al. . |
| 4,058,400 | 11/1977 | Crivello . |
| 4,067,892 | 1/1978 | Thorne et al. . |
| 4,071,424 | 1/1978 | Dart et al. . |
| 4,073,968 | 2/1978 | Miyamoto et al. . |
| 4,077,769 | 3/1978 | Garcia . |
| 4,079,183 | 3/1978 | Green . |
| 4,085,062 | 4/1978 | Virgilio et al. . |
| 4,090,877 | 5/1978 | Streeper . |
| 4,100,047 | 7/1978 | McCarty . |
| 4,105,572 | 8/1978 | Gorondy . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,126,412 | 11/1978 | Masson et al. . |
| 4,132,562 | 1/1979 | Burke, Jr. . |
| 4,141,807 | 2/1979 | Via . |
| 4,144,156 | 3/1979 | Kuesters et al. . |
| 4,148,658 | 4/1979 | Kondoh et al. . |
| 4,162,162 | 7/1979 | Dueber . |
| 4,171,977 | 10/1979 | Hasegawa et al. . |
| 4,179,577 | 12/1979 | Green . |
| 4,181,807 | 1/1980 | Green . |
| 4,190,671 | 2/1980 | Vanstone et al. . |
| 4,197,080 | 4/1980 | Mee . |
| 4,199,420 | 4/1980 | Photis . |
| 4,229,172 | 10/1980 | Baumann et al. . |
| 4,232,106 | 11/1980 | Iwasaki et al. . |
| 4,238,492 | 12/1980 | Majoie . |
| 4,239,843 | 12/1980 | Hara et al. . |
| 4,239,850 | 12/1980 | Kita et al. . |
| 4,241,155 | 12/1980 | Hara et al. . |
| 4,242,430 | 12/1980 | Hara et al. . |
| 4,242,431 | 12/1980 | Hara et al. . |
| 4,245,018 | 1/1981 | Hara et al. . |
| 4,245,033 | 1/1981 | Eida et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,251,662 | 2/1981 | Ozawa et al. . |
| 4,254,195 | 3/1981 | Hara et al. . |
| 4,256,493 | 3/1981 | Yokoyama et al. . |
| 4,256,817 | 3/1981 | Hara et al. . |
| 4,258,123 | 3/1981 | Nagashima et al. . |
| 4,258,367 | 3/1981 | Mansukhani . |
| 4,259,432 | 3/1981 | Kondoh et al. . |
| 4,262,936 | 4/1981 | Miyamoto . |
| 4,268,605 | 5/1981 | Hara et al. . |
| 4,268,667 | 5/1981 | Anderson . |
| 4,269,926 | 5/1981 | Hara et al. . |
| 4,270,130 | 5/1981 | Houle et al. . |
| 4,271,252 | 6/1981 | Hara et al. . |
| 4,271,253 | 6/1981 | Hara et al. . |
| 4,272,244 | 6/1981 | Schlick . |
| 4,276,211 | 6/1981 | Singer et al. . |
| 4,277,497 | 7/1981 | Fromantin . |
| 4,279,653 | 7/1981 | Makishima et al. . |
| 4,279,982 | 7/1981 | Iwasaki et al. . |
| 4,279,985 | 7/1981 | Nonogaki et al. . |
| 4,284,485 | 8/1981 | Berner . |
| 4,288,631 | 9/1981 | Ching . |
| 4,289,844 | 9/1981 | Specht et al. . |
| 4,290,870 | 9/1981 | Kondoh et al. . |
| 4,293,458 | 10/1981 | Gruenberger et al. . |
| 4,298,679 | 11/1981 | Shinozaki et al. . |
| 4,300,123 | 11/1981 | McMillin et al. . |
| 4,301,223 | 11/1981 | Nakamura et al. . |
| 4,302,606 | 11/1981 | Barabas et al. . |
| 4,306,014 | 12/1981 | Kunikane et al. . |
| 4,307,182 | 12/1981 | Dalzell et al. . |
| 4,308,400 | 12/1981 | Felder et al. . |
| 4,315,807 | 2/1982 | Felder et al. . |
| 4,318,705 | 3/1982 | Nowak et al. . |
| 4,318,791 | 3/1982 | Felder et al. . |
| 4,321,118 | 3/1982 | Felder et al. . |
| 4,335,054 | 6/1982 | Blaser et al. . |
| 4,335,055 | 6/1982 | Blaser et al. . |
| 4,336,323 | 6/1982 | Winslow . |
| 4,343,891 | 8/1982 | Aasen et al. . |
| 4,345,011 | 8/1982 | Drexhage . |
| 4,347,111 | 8/1982 | Gehlhaus et al. . |
| 4,349,617 | 9/1982 | Kawashiri et al. . |
| 4,350,753 | 9/1982 | Shelnut et al. . |
| 4,351,893 | 9/1982 | Anderson . |
| 4,356,247 | * 10/1982 | Aotani et al. . |
| 4,356,255 | 10/1982 | Tachikawa et al. . |
| 4,357,468 | 11/1982 | Szejtli et al. . |
| 4,359,524 | 11/1982 | Masuda et al. . |
| 4,362,806 | 12/1982 | Whitmore . |
| 4,367,072 | 1/1983 | Vogtle et al. . |
| 4,367,280 | 1/1983 | Kondo et al. . |
| 4,369,283 | 1/1983 | Altschuler . |

| | | |
|---|---|---|
| 4,370,401 | 1/1983 | Winslow et al. . |
| 4,372,582 | 2/1983 | Geisler . |
| 4,373,017 | 2/1983 | Masukawa et al. . |
| 4,373,020 | 2/1983 | Winslow . |
| 4,374,984 | 2/1983 | Eichler et al. . |
| 4,376,887 | 3/1983 | Greenaway et al. . |
| 4,383,835 | 5/1983 | Preuss et al. . |
| 4,390,616 | 6/1983 | Sato et al. . |
| 4,391,867 | 7/1983 | Derick et al. . |
| 4,399,209 | 8/1983 | Sanders et al. . |
| 4,400,173 | 8/1983 | Beavan . |
| 4,401,470 | 8/1983 | Bridger . |
| 4,416,961 | 11/1983 | Drexhage . |
| 4,421,559 | 12/1983 | Owatari . |
| 4,424,325 | 1/1984 | Tsunoda et al. . |
| 4,425,162 | 1/1984 | Sugiyama . |
| 4,425,424 | 1/1984 | Altland et al. . |
| 4,426,153 | 1/1984 | Libby et al. . |
| 4,434,035 | 2/1984 | Eichler et al. . |
| 4,440,827 | 4/1984 | Miyamoto et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,477,681 | 10/1984 | Gehlhaus et al. . |
| 4,489,334 | 12/1984 | Owatari . |
| 4,495,041 | 1/1985 | Goldstein . |
| 4,496,447 | 1/1985 | Eichler et al. . |
| 4,500,355 | 2/1985 | Shimada et al. . |
| 4,508,570 | 4/1985 | Fugii et al. . |
| 4,510,392 | 4/1985 | Litt et al. . |
| 4,523,924 | 6/1985 | Lacroix . |
| 4,524,122 | 6/1985 | Weber et al. . |
| 4,534,838 | 8/1985 | Lin et al. . |
| 4,548,896 | 10/1985 | Sabongi et al. . |
| 4,555,474 | 11/1985 | Kawamura . |
| 4,557,730 | 12/1985 | Bennett et al. . |
| 4,559,371 * | 12/1985 | Husler et al. . |
| 4,564,560 | 1/1986 | Tani et al. . |
| 4,565,769 | 1/1986 | Dueber et al. . |
| 4,567,171 | 1/1986 | Mangum . |
| 4,571,377 | 2/1986 | McGinniss et al. . |
| 4,582,862 * | 4/1986 | Berner et al. . |
| 4,595,745 | 6/1986 | Nakano et al. . |
| 4,604,344 | 8/1986 | Irving et al. . |
| 4,605,442 | 8/1986 | Kawashita et al. . |
| 4,613,334 | 9/1986 | Thomas et al. . |
| 4,614,723 | 9/1986 | Schmidt et al. . |
| 4,617,380 | 10/1986 | Hinson et al. . |
| 4,620,875 | 11/1986 | Shimada et al. . |
| 4,620,876 | 11/1986 | Fugii et al. . |
| 4,622,286 | 11/1986 | Sheets . |
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,711,802 | 12/1987 | Tannenbaum . |
| 4,713,113 | 12/1987 | Shimada et al. . |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al . |
| 4,895,880 | 1/1990 | Gootschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,944,988 | 7/1990 | Yasuda et al. . |
| 4,950,304 | 8/1990 | Reinert et al. . |

| | | | | | |
|---|---|---|---|---|---|
| 4,952,478 | 8/1990 | Miyagawa et al. . | 5,144,964 | 9/1992 | Demian . |
| 4,952,680 | 8/1990 | Schmeidl . | 5,147,901 | 9/1992 | Rutsch et al. . |
| 4,954,380 | 9/1990 | Kanome et al. . | 5,153,104 | 10/1992 | Rossman et al. . |
| 4,954,416 | 9/1990 | Wright et al. . | 5,153,105 | 10/1992 | Sher et al. . |
| 4,956,254 | 9/1990 | Washizu et al. . | 5,153,166 | 10/1992 | Jain et al. . |
| 4,964,871 | 10/1990 | Reinert et al. . | 5,160,346 | 11/1992 | Fuso et al. . |
| 4,965,294 | 10/1990 | Ohngemach et al. . | 5,160,372 | 11/1992 | Matrick . |
| 4,966,607 | 10/1990 | Shinoki et al. . | 5,166,041 | 11/1992 | Murofushi et al. . |
| 4,966,833 | 10/1990 | Inoue . | 5,169,436 | 12/1992 | Matrick . |
| 4,968,596 | 11/1990 | Inoue et al. . | 5,169,438 | 12/1992 | Matrick . |
| 4,968,813 | 11/1990 | Rule et al. . | 5,173,112 | 12/1992 | Matrick et al. . |
| 4,985,345 | 1/1991 | Hayakawa et al. . | 5,176,984 | 1/1993 | Hipps, Sr. et al. . |
| 4,987,056 | 1/1991 | Imahashi et al. . | 5,178,420 | 1/1993 | Shelby . |
| 4,988,561 | 1/1991 | Wason . | 5,180,425 | 1/1993 | Matrick et al. . |
| 4,997,745 | 3/1991 | Kawamura et al. . | 5,180,624 | 1/1993 | Kojima et al. . |
| 5,001,330 | 3/1991 | Koch . | 5,180,652 | 1/1993 | Yamaguchi et al. . |
| 5,002,853 | 3/1991 | Aoai et al. . | 5,181,935 | 1/1993 | Reinert et al. . |
| 5,002,993 | 3/1991 | West et al. . | 5,185,236 | 2/1993 | Shiba et al. . |
| 5,003,142 | 3/1991 | Fuller . | 5,187,045 | 2/1993 | Bonham et al. . |
| 5,006,758 | 4/1991 | Gellert et al. . | 5,187,049 | 2/1993 | Sher et al. . |
| 5,013,959 | 5/1991 | Kogelschatz . | 5,190,565 | 3/1993 | Berenbaum et al. . |
| 5,017,195 | 5/1991 | Satou et al. . | 5,190,710 | 3/1993 | Kletecka . |
| 5,023,129 | 6/1991 | Morganti et al. . | 5,190,845 | 3/1993 | Hashimoto et al. . |
| 5,025,036 | 6/1991 | Carson et al. . | 5,193,854 | 3/1993 | Borowski, Jr. et al. . |
| 5,026,425 | 6/1991 | Hindagolla et al. . | 5,196,295 | 3/1993 | Davis . |
| 5,026,427 | 6/1991 | Mitchell et al. . | 5,197,991 | 3/1993 | Rembold . |
| 5,028,262 | 7/1991 | Barlow, Jr. et al. . | 5,198,330 | 3/1993 | Martic et al. . |
| 5,028,792 | 7/1991 | Mullis . | 5,202,209 | 4/1993 | Winnik et al. . |
| 5,030,243 | 7/1991 | Reinert . | 5,202,210 | 4/1993 | Matsuoka et al. . |
| 5,030,248 | 7/1991 | Meszaros . | 5,202,211 | 4/1993 | Vercoulen . |
| 5,034,526 | 7/1991 | Bonham et al. . | 5,202,212 | 4/1993 | Shin et al. . |
| 5,037,726 | 8/1991 | Kojima et al. . | 5,202,213 | 4/1993 | Nakahara et al. . |
| 5,045,435 | 9/1991 | Adams et al. . | 5,202,215 | 4/1993 | Kanakura et al. . |
| 5,045,573 | 9/1991 | Kohler et al. . | 5,202,221 | 4/1993 | Imai et al. . |
| 5,047,556 | 9/1991 | Kohler et al. . | 5,205,861 | 4/1993 | Matrick . |
| 5,049,777 | 9/1991 | Mechtersheimer . | 5,208,136 | 5/1993 | Zanoni et al. . |
| 5,053,320 | 10/1991 | Robbillard . | 5,209,814 | 5/1993 | Felten et al. . |
| 5,055,579 | 10/1991 | Pawlowski et al. . | 5,219,703 | 6/1993 | Bugner et al. . |
| 5,057,562 | 10/1991 | Reinert . | 5,221,334 | 6/1993 | Ma et al. . |
| 5,068,140 | 11/1991 | Malhotra et al. . | 5,224,197 | 6/1993 | Zanoni et al. . |
| 5,068,364 | 11/1991 | Takagaki et al. . | 5,224,476 | 7/1993 | Schultz et al. . |
| 5,069,681 | 12/1991 | Bouwknegt et al. . | 5,224,987 | 7/1993 | Matrick . |
| 5,070,001 | 12/1991 | Stahlhofen . | 5,226,957 | 7/1993 | Wickramanayake et al. . |
| 5,073,448 | 12/1991 | Vieira et al. . | 5,227,022 | 7/1993 | Leonhardt et al. . |
| 5,074,885 | 12/1991 | Reinert . | 5,230,982 | 7/1993 | Davis et al. . |
| 5,076,808 | 12/1991 | Hahn et al. . | 5,241,059 | 8/1993 | Yoshinaga . |
| 5,077,402 * | 12/1991 | Desobry et al. . | 5,250,109 | 10/1993 | Chan et al. . |
| 5,085,698 | 2/1992 | Ma et al. . | 5,254,429 | 10/1993 | Gracia et al. . |
| 5,087,550 | 2/1992 | Blum et al. . | 5,256,193 | 10/1993 | Winnik et al. . |
| 5,089,050 | 2/1992 | Vieira et al. . | 5,258,274 | 11/1993 | Helland et al. . |
| 5,089,374 | 2/1992 | Saeva . | 5,261,953 | 11/1993 | Vieira et al. . |
| 5,096,456 | 3/1992 | Reinert et al. . | 5,262,276 | 11/1993 | Kawamura . |
| 5,096,489 | 3/1992 | Laver . | 5,268,027 | 12/1993 | Chan et al. . |
| 5,096,781 | 3/1992 | Vieira et al. . | 5,270,078 | 12/1993 | Walker et al. . |
| 5,098,477 | 3/1992 | Vieira et al. . | 5,271,764 | 12/1993 | Winnik et al. . |
| 5,098,793 | 3/1992 | Rohrbach et al. . | 5,271,765 | 12/1993 | Ma . |
| 5,098,806 | 3/1992 | Robillard . | 5,272,201 | 12/1993 | Ma et al. . |
| 5,106,723 | 4/1992 | West et al. . | 5,275,646 | 1/1994 | Marshall et al. . |
| 5,108,505 | 4/1992 | Moffat . | 5,279,652 | 1/1994 | Kaufmann et al. . |
| 5,108,874 | 4/1992 | Griffing et al. . | 5,282,894 | 2/1994 | Albert et al. . |
| 5,110,706 | 5/1992 | Yumoto et al. . | 5,284,734 | 2/1994 | Blum et al. . |
| 5,110,709 | 5/1992 | Aoai et al. . | 5,286,286 | 2/1994 | Winnik et al. . |
| 5,114,832 | 5/1992 | Zertani et al. . | 5,286,288 | 2/1994 | Tobias et al. . |
| 5,124,723 | 6/1992 | Laver . | 5,294,528 | 3/1994 | Furutachi . |
| 5,130,227 | 7/1992 | Wade et al. . | 5,296,275 | 3/1994 | Goman et al. . |
| 5,133,803 | 7/1992 | Moffatt . | 5,296,556 | 3/1994 | Frihart . |
| 5,135,940 | 8/1992 | Belander et al. . | 5,298,030 | 3/1994 | Burdeska et al. . |
| 5,139,572 | 8/1992 | Kawashima . | 5,300,403 | 4/1994 | Angelopolus et al. . |
| 5,139,687 | 8/1992 | Borgher, Sr. et al. . | 5,300,654 | 4/1994 | Nakajima et al. . |
| 5,141,556 | 8/1992 | Matrick . | 5,302,195 | 4/1994 | Helbrecht . |
| 5,141,797 | 8/1992 | Wheeler . | 5,302,197 | 4/1994 | Wickramanayake et al. . |

| | | | | | | |
|---|---|---|---|---|---|---|
| 5,310,778 | 5/1994 | Shor et al. . | | 5,686,503 | 11/1997 | Nohr et al. . |
| 5,312,713 | 5/1994 | Yokoyama et al. . | | 5,700,582 | 12/1997 | Sargeant et al. . |
| 5,312,721 | 5/1994 | Gesign . | | 5,700,850 | 12/1997 | Nohr et al. . |
| 5,324,349 | 6/1994 | Sano et al. . | | 5,705,247 | 1/1998 | Arai et al. . |
| 5,328,504 | 7/1994 | Ohnishi . | | 5,709,955 | 1/1998 | Nohr et al. . |
| 5,330,860 | 7/1994 | Grot et al. . | | 5,709,976 | 1/1998 | Malhotra . |
| 5,334,455 | 8/1994 | Noren et al. . | | 5,721,287 | 2/1998 | Nohr et al. . |
| 5,338,319 | 8/1994 | Kaschig et al. . | | 5,733,693 | 3/1998 | Nohr et al. . |
| 5,340,631 | 8/1994 | Matsuzawa et al. . | | 5,738,932 | 4/1998 | Kondo et al. . |
| 5,340,854 | 8/1994 | Martic et al. . | | 5,739,175 | 4/1998 | Nohr et al. . |
| 5,344,483 | 9/1994 | Hinton . | | 5,747,550 | 5/1998 | Nohr et al. . |
| 5,356,464 | 10/1994 | Hickman et al. . | | 5,773,182 | 6/1998 | Nohr et al. . |
| 5,362,592 | 11/1994 | Murofushi et al. . | | 5,782,963 | 7/1998 | Nohr et al. . |
| 5,362,916 * | 11/1994 | Edwards et al. . | | 5,786,132 | 7/1998 | Nohr et al. . |
| 5,368,689 | 11/1994 | Agnemo . | | 5,798,015 | 8/1998 | Nohr et al. . |
| 5,372,387 | 12/1994 | Wajda . | | 5,811,199 | 9/1998 | MacDonald et al. . |
| 5,372,917 | 12/1994 | Tsuchida et al. . | | 5,837,429 | 11/1998 | Nohr et al. . |
| 5,374,335 | 12/1994 | Lindgren et al. . | | 5,849,411 | 12/1998 | Nohr et al. . |
| 5,376,503 | 12/1994 | Audett et al. . | | 5,855,655 | 1/1999 | Nohr et al. . |
| 5,383,961 | 1/1995 | Bauer et al. . | | 5,865,471 | 2/1999 | Nohr et al. . |
| 5,384,186 | 1/1995 | Trinh . | | 5,883,161 | 3/1999 | Wood et al. . |
| 5,393,580 | 2/1995 | Ma et al. . | | 5,885,337 | 3/1999 | Nohr et al. . |
| 5,401,303 | 3/1995 | Stoffel et al. . | | 5,891,229 | 4/1999 | Nohr et al. . |
| 5,401,562 | 3/1995 | Akao . | | 5,911,855 | 6/1999 | Dransmann et al. . |
| 5,415,686 | 5/1995 | Kurabayashi et al. . | | 6,022,906 * | 2/2000 | Ohwa et al. . |
| 5,415,976 | 5/1995 | Ali . | | | | |
| 5,424,407 | 6/1995 | Tanaka et al. . | | FOREIGN PATENT DOCUMENTS | | |
| 5,425,978 | 6/1995 | Berneth et al. . | | 2053094 | 4/1992 | (CA) . |
| 5,426,164 | 6/1995 | Babb et al. . | | 603767 | 8/1978 | (CH) . |
| 5,427,415 | 6/1995 | Chang . | | 197808 | 5/1988 | (CH) . |
| 5,429,628 | 7/1995 | Trinh et al. . | | 94118 | 5/1958 | (CZ) . |
| 5,431,720 | 7/1995 | Nagai et al. . | | 1047787 | 12/1957 | (DE) . |
| 5,432,274 | 7/1995 | Luong et al. . | | 1022801 | 1/1958 | (DE) . |
| 5,445,651 | 8/1995 | Thoen et al. . | | 1039835 | 9/1958 | (DE) . |
| 5,445,842 | 8/1995 | Tanaka et al. . | | 1040562 | 10/1958 | (DE) . |
| 5,455,074 | 10/1995 | Nohr et al. . | | 1045414 | 12/1958 | (DE) . |
| 5,455,143 | 10/1995 | Ali . | | 1047013 | 12/1958 | (DE) . |
| 5,459,014 | 10/1995 | Nishijima et al. . | | 1132540 | 7/1962 | (DE) . |
| 5,464,472 | 11/1995 | Horn et al. . | | 1154069 | 9/1963 | (DE) . |
| 5,466,283 | 11/1995 | Kondo et al. . | | 1240811 | 5/1967 | (DE) . |
| 5,474,691 | 12/1995 | Severns . | | 2202497 | 8/1972 | (DE) . |
| 5,475,080 | 12/1995 | Gruber et al. . | | 2432563 | 2/1975 | (DE) . |
| 5,476,540 | 12/1995 | Shields et al. . | | 2437380 | 2/1975 | (DE) . |
| 5,479,949 | 1/1996 | Battard et al. . | | 2444520 | 3/1975 | (DE) . |
| 5,489,503 | 2/1996 | Toan . | | 2416259 | 10/1975 | (DE) . |
| 5,498,345 | 3/1996 | Jollenbeck et al. . | | 2714978 | 10/1977 | (DE) . |
| 5,501,774 | 3/1996 | Burke . | | 2722264 | 11/1978 | (DE) . |
| 5,501,902 | 3/1996 | Kronzer . | | 158237 | 1/1983 | (DE) . |
| 5,503,664 | 4/1996 | Sano et al. . | | 3126433 | 1/1983 | (DE) . |
| 5,509,957 | 4/1996 | Toan et al. . | | 3415033 | 10/1984 | (DE) . |
| 5,531,821 | 7/1996 | Wu . | | 271512 | 9/1989 | (DE) . |
| 5,532,112 | 7/1996 | Kohler et al. . | | 3921600 | 1/1990 | (DE) . |
| 5,541,633 | 7/1996 | Winnik et al. . | | 3833437 | 4/1990 | (DE) . |
| 5,543,459 | 8/1996 | Hartmann et al. . | | 3833438 | 4/1990 | (DE) . |
| 5,569,529 | 10/1996 | Becker et al. . | | 004036328 | 7/1991 | (DE) . |
| 5,571,313 | 11/1996 | Mafune et al. . | | 4132288 | 4/1992 | (DE) . |
| 5,575,891 | 11/1996 | Trokhan et al. . | | 4126461 | 2/1993 | (DE) . |
| 5,580,369 | 12/1996 | Belding et al. . | | 0003884 | 9/1979 | (EP) . |
| 5,591,489 | 1/1997 | Dragner et al. . | | 0029284 | 5/1981 | (EP) . |
| 5,597,405 | 1/1997 | Grigoryan et al. . | | 0127574 | 12/1984 | (EP) . |
| 5,607,803 | 3/1997 | Murofushi et al. . | | 0 209 831 | 1/1987 | (EP) . |
| 5,616,443 | 4/1997 | Nohr et al. . | | 0223587 | 5/1987 | (EP) . |
| 5,635,297 | 6/1997 | Ogawa et al. . | | 0262533 | 4/1988 | (EP) . |
| 5,643,356 | 7/1997 | Nohr et al. . | | 0280458 | 8/1988 | (EP) . |
| 5,643,631 | 7/1997 | Donigian et al. . | | 0 303 803 | 2/1989 | (EP) . |
| 5,643,701 | 7/1997 | Nohr et al. . | | 0308274 | 3/1989 | (EP) . |
| 5,645,964 | 7/1997 | Nohr et al. . | | 0351615 | 1/1990 | (EP) . |
| 5,672,392 | 9/1997 | De Clercq et al. . | | 0371304 | 6/1990 | (EP) . |
| 5,681,380 | 10/1997 | Nohr et al. . | | 0373662 | 6/1990 | (EP) . |
| 5,683,843 | 11/1997 | Nohr et al. . | | 0375160 | 6/1990 | (EP) . |
| 5,685,754 | 11/1997 | Nohr et al. . | | 0390439 | 10/1990 | (EP) . |

| | | | | | | |
|---|---|---|---|---|---|---|
| 0458140A1 | 10/1991 | (EP) . | | 613781 | 1/1986 | (JP) . |
| 0458140 | 11/1991 | (EP) . | | 61-25885 | 2/1986 | (JP) . |
| 0468465 | 1/1992 | (EP) . | | 61-30592 | 2/1986 | (JP) . |
| 0 469 595 | 2/1992 | (EP) . | | 61-40366 | 2/1986 | (JP) . |
| 0 475 075 | 3/1992 | (EP) . | | 61-77846 | 4/1986 | (JP) . |
| 0542286 | 5/1993 | (EP) . | | 61-128973 | 6/1986 | (JP) . |
| 000571190 | 11/1993 | (EP) . | | 61-97025 | 9/1986 | (JP) . |
| 0 605 840 | 7/1994 | (EP) . | | 61-222789 | 10/1986 | (JP) . |
| 0608433 | 8/1994 | (EP) . | | 61-247703 | 11/1986 | (JP) . |
| 0609159 | 8/1994 | (EP) . | | 61-285403 | 12/1986 | (JP) . |
| 0 635 380 | 1/1995 | (EP) . | | 627703 | 1/1987 | (JP) . |
| 0639664 | 2/1995 | (EP) . | | 62-100557 | 5/1987 | (JP) . |
| 0 673 779 | 9/1995 | (EP) . | | 62-97881 | 5/1987 | (JP) . |
| 0 716 929 | 6/1996 | (EP) . | | 62127281 | 6/1987 | (JP) . |
| 0 737 592 | 10/1996 | (EP) . | | 63-43959 | 2/1988 | (JP) . |
| 0755984 | 1/1997 | (EP) . | | 63-48370 | 3/1988 | (JP) . |
| 0 805 152 | 11/1997 | (EP) . | | 6395439 | 4/1988 | (JP) . |
| 0 861 880 | 9/1998 | (EP) . | | 6395440 | 4/1988 | (JP) . |
| 2245010 | 4/1975 | (FR) . | | 6395445 | 4/1988 | (JP) . |
| 2383157 | 10/1978 | (FR) . | | 6395446 | 4/1988 | (JP) . |
| 275245 | 10/1928 | (GB) . | | 6395447 | 4/1988 | (JP) . |
| 349339 | 5/1931 | (GB) . | | 6395448 | 4/1988 | (JP) . |
| 355686 | 8/1931 | (GB) . | | 6395449 | 4/1988 | (JP) . |
| 399753 | 10/1933 | (GB) . | | 6395450 | 4/1988 | (JP) . |
| 441085 | 1/1936 | (GB) . | | 63151946 | 6/1988 | (JP) . |
| 463515 | 4/1937 | (GB) . | | 63-164953 | 7/1988 | (JP) . |
| 492711 | 9/1938 | (GB) . | | 63-165498 | 7/1988 | (JP) . |
| 518612 | 3/1940 | (GB) . | | 63-223077 | 9/1988 | (JP) . |
| 539912 | 9/1941 | (GB) . | | 63-223078 | 9/1988 | (JP) . |
| 626727 | 7/1947 | (GB) . | | 63-243101 | 10/1988 | (JP) . |
| 600451 | 4/1948 | (GB) . | | 63-199781 | 12/1988 | (JP) . |
| 616362 | 1/1949 | (GB) . | | 64-15049 | 1/1989 | (JP) . |
| 618616 | 2/1949 | (GB) . | | 6429337 | 1/1989 | (JP) . |
| 779389 | 7/1957 | (GB) . | | 64-40948 | 2/1989 | (JP) . |
| 1150987 | 5/1969 | (GB) . | | 89014948 | 3/1989 | (JP) . |
| 1372884 | 11/1974 | (GB) . | | 1-128063 | 5/1989 | (JP) . |
| 2146357 | 4/1985 | (GB) . | | 1146974 | 6/1989 | (JP) . |
| 662500 | 4/1964 | (IT) . | | 01210477 | 8/1989 | (JP) . |
| 4315663 | 7/1968 | (JP) . | | 1288854 | 11/1989 | (JP) . |
| 4726653 | 7/1972 | (JP) . | | 2-58573 | 2/1990 | (JP) . |
| 4745409 | 11/1972 | (JP) . | | 292957 | 4/1990 | (JP) . |
| 49-8909 | 2/1974 | (JP) . | | 2179642 | 7/1990 | (JP) . |
| 5065592 | 6/1975 | (JP) . | | 2282261 | 11/1990 | (JP) . |
| 51-17802 | 2/1976 | (JP) . | | 3-134072 | 6/1991 | (JP) . |
| 53-104321 | 9/1978 | (JP) . | | 03163566 | 7/1991 | (JP) . |
| 55-62059 | 5/1980 | (JP) . | | 3-170415 | 7/1991 | (JP) . |
| 55-90506 | 7/1980 | (JP) . | | 3-206439 | 9/1991 | (JP) . |
| 56-8134 | 1/1981 | (JP) . | | 3-258867 | 11/1991 | (JP) . |
| 0014233 | 2/1981 | (JP) . | | 3-203694 | 12/1991 | (JP) . |
| 5614569 | 2/1981 | (JP) . | | 3284668 | 12/1991 | (JP) . |
| 56-24472 | 3/1981 | (JP) . | | 4023884 | 1/1992 | (JP) . |
| 56-36556 | 4/1981 | (JP) . | | 4023885 | 1/1992 | (JP) . |
| 5761055 | 4/1982 | (JP) . | | 4-45174 | 2/1992 | (JP) . |
| 57128283 | 8/1982 | (JP) . | | 4100801 | 4/1992 | (JP) . |
| 57171775 | 10/1982 | (JP) . | | 4-136075 | 5/1992 | (JP) . |
| 424756 | 2/1983 | (JP) . | | 04356087 | 12/1992 | (JP) . |
| 58-124452 | 7/1983 | (JP) . | | 543806 | 2/1993 | (JP) . |
| 58-125770 | 7/1983 | (JP) . | | 561220 | 3/1993 | (JP) . |
| 58-222164 | 12/1983 | (JP) . | | 5080506 | 4/1993 | (JP) . |
| 5989360 | 5/1984 | (JP) . | | 05119506 | 5/1993 | (JP) . |
| 29219270 | 12/1984 | (JP) . | | 5134447 | 5/1993 | (JP) . |
| 59-219270 | 4/1985 | (JP) . | | 5-140498 | 6/1993 | (JP) . |
| 60-192729 | 10/1985 | (JP) . | | 2-219869 | 9/1993 | (JP) . |
| 60239739 | 11/1985 | (JP) . | | 5263067 | 10/1993 | (JP) . |
| 60239740 | 11/1985 | (JP) . | | 680915 | 3/1994 | (JP) . |
| 60239741 | 11/1985 | (JP) . | | 6116555 | 4/1994 | (JP) . |
| 60239743 | 11/1985 | (JP) . | | 6116556 | 4/1994 | (JP) . |
| 61-14994 | 1/1986 | (JP) . | | 6116557 | 4/1994 | (JP) . |
| 61-14995 | 1/1986 | (JP) . | | 6-175584 | 6/1994 | (JP) . |
| 61-21184 | 1/1986 | (JP) . | | 6214339 | 8/1994 | (JP) . |
| 61-288 | 1/1986 | (JP) . | | 6256494 | 9/1994 | (JP) . |

| | | |
|---|---|---|
| 6256633 | 9/1994 | (JP) . |
| 7113828 | 4/1972 | (NL) . |
| 1310767 | 5/1987 | (RU) . |
| 1772118 | 10/1992 | (SU) . |
| 92/11295 | 7/1992 | (WO) . |
| 93/06597 | 4/1993 | (WO) . |
| 94/01503 | 1/1994 | (WO) . |
| 94/22500 | 10/1994 | (WO) . |
| 94/22501 | 10/1994 | (WO) . |
| 95/04955 | 2/1995 | (WO) . |
| 95/28285 | 10/1995 | (WO) . |
| 96/00740 | 1/1996 | (WO) . |
| 96/19502 | 6/1996 | (WO) . |
| 96/22335 | 7/1996 | (WO) . |
| 96/24636 | 8/1996 | (WO) . |
| 97/20000 | 6/1997 | (WO) . |
| 97/35933 | 10/1997 | (WO) . |
| 98/23695 | 6/1998 | (WO) . |

OTHER PUBLICATIONS

Derwent Publications Ltd., London, JP 05297627 (Fujitsu Ltd.), Nov. 12, 1993. (Abstract).
Patent Abstracts of Japan, JP 5241369 (Bando Chem Ind Ltd et al.), Sep. 21, 1993. (Abstract).
Derwent Publications Ltd., London, JP 05232738 (Yamazaki, T.), Sep. 10, 1993. (Abstract).
Derwent Publications Ltd., London, EP 000559310 (Zeneca Ltd.), Sep. 8, 1993. (Abstract).
Derwent Publications Ltd., London, J,A, 5–230410 (Seiko Epson Corp), Sep. 7, 1993. (Abstract).
Derwent Publications, Ltd., London, JP 5–230407 (Mitsubishi Kasei Corp), Sep. 7, 1993. (Abstract).
Abstract Of Patent, JP 405230410 (Seiko Epson Corp.), Sep. 7, 1993. Abstract 1993.
Abstract Of Patent, JP 405230407 (Mitsubishi Kasei Corp.), Sep. 7, 1993. (Abstract).
Patent Abstracts of Japan, JP 5197198 (Bando Chem Ind Ltd et al.), Aug. 6, 1993. (Abstract).
Database WPI—Derwent Publications Ltd., London, J.A. 5197069 (Bando Chem), Aug. 6, 1993. (Abstract).
Abstract of patent, JP 5–195450 (Nitto Boseki Co. Ltd), Aug. 3, 1993.
Derwent World Patents Index JP 5186725 (Seiko Epson Corp.), Jul. 27, 1993. abstract.
Patent Abstracts of Japan, JP 5181308 (Bando Chem Ind Ltd et al.), Jul. 23, 1993. (Abstract).
Patent Abstracts of Japan, JP 5181310 (Bando Chem Ind Ltd et al.), Jul. 23, 1993. (Abstract).
Derwent Publications Ltd., London, JP 5–132638 (Mitsubishi Kasei Corp), May 28, 1993. (Abstract).
Abstract of Patent, JP 405132638 (Mitsubishi Kasei Corp.), May 28, 1993. (Abstract).
Derwent Publications Ltd., London, JP 5–125318 (Mitsubishi Kasei Corp), May 21, 1993. (Abstract).
Abstract Of Patent, JP 405125318 (Mitsubishi Kasei Corp.), May 21, 1993. (Abstract).
Abstract of patent, JP 05–117200 (Hidefumi Hirai et al.) (May 14, 1993).
Derwent World Patents Index, JP 5117105 (Mitsui Toatsu Chem Inc.) May 14, 1993.
Derwent Publications Ltd., London, JP 05061246 (Ricoh KK), Mar. 12, 1993. (Abstract).
Husain N. et al. "Cyclodextrins as mobile–phase additives in reversed–phase HPLC" *American Laboratory* 82 80–87.
Hamilton, D.P. "Tired of Shredding? New Ricoh Method Tries Different Tack" *Wall Street Journal* B2 1993.

"Cyclodextrins: A Breakthrough for Molecular Encapsulation" *American Maize Products Co.* (*AMAIZO*) 1993.
Duxbury "The Photochemistry and Photophysics of Triphenylmethane Dyes in Solid Liquid Media" *Chemical Review* 93 381–433 1993.
Abstract of patent, JP 04–351603 (Dec. 7, 1992).
Abstract of patent, JP 04–351602 1992.
Derwent Publications Ltd., London, JP 404314769 (Citizen Watch Co. Ltd.), Nov. 5, 1992. (Abstract).
Abstract of patent, JP 04315739 1992.
Derwent Publications Ltd., London, JP 04300395 (Funai Denki KK), Oct. 23, 1992. (Abstract).
Derwent Publications Ltd., London, JP 404213374 (Mitsubishi Kasei Corp), Aug. 4, 1992. (Abstract).
Abstract of patent, JP 04–210228 1992.
Abstract Of Patent, JP 404202571 (Canon Inc.), Jul. 23, 1992. (Abstract).
Abstract Of Patent, JP 404202271 (Mitsubishi Kasei Corp.), Jul. 23, 1992. (Abstract).
Derwent WPI, JP 4–197657 (Toshiba KK) Jul. 17, 1992, abstract.
Derwent Publications Ltd., London, JP 4–189877 (Seiko Epson Corp), Jul. 8, 1992. (Abstract).
Derwent Publications Ltd., London, JP 404189876 (Seiko Epson Corp), Jul. 8, 1992. (Abstract).
Abstract Of Patent, JP 404189877 (Seiko Epson Corp.), Jul. 8. 1992. (Abstract).
Derwent Publications Ltd., London, J.A. 4–170479 (Seiko Epson Corp), Jun. 18, 1992. (Abstract).
Abstract of patent, JP 04–81402 1992.
Abstract of patent, JP 04–81401 1992.
Kogelschatz "Silent–discharge drive excimer UV sources and their applications" *Applied Surface Science* 410–423 (1992.
Derwent Publications, Ltd., London, JP 403269167 (Japan Wool Textile KK), Nov. 29, 1991 (Abstract).
Derwent Publications Ltd., London, JO 3247676 (Canon KK), Nov. 5, 1991 (Abstract).
Abstract of patent, JP 03–220384 1991.
Patent Abstracts of Japan, JP 03184896 (Dainippon Printing Co Ltd.) Aug. 12, 1991.
Derwent Publications Ltd., London, JP 3167270 (Mitsubishi Kasei Corp), Jul. 19, 1991. (Abstract).
Derwent Publications Ltd., London, JO 3167270 (Mitsubishi Kasei Corp.), Jul. 19, 1991 (Abstract).
Derwent World Patents Index EP 435536 (Canon KK) Jul. 3, 1991. abstract.
Derwent Publications Ltd., London, JO 3093870 (Dainippon Ink Chem KK.), Apr. 18, 1991 (Abstract).
Abstract of patent, JP 06369890 1991.
Kogelschatz, U. et al. "New Excimer UV Sources for Industrial Applications" *ABB Review* 391 1–10 1991.
Abstract of patent, JP 03–41165 1991.
"Coloring/Decoloring Agent for Tonor Use Developed" *Japan Chemical Week* 1991.
Braithwaite, M., et al. "Formulation" *Chemistry & Technology of UV & EB Formulation for Coatings, Inks & Paints* IV 11–12 1991.
Scientific Polymer Products, Inc. Brochure 24–31 1991.
Dietliker, K. "Photoiniators for Free Radical and Catioinc Polymerisation" *Chem. & Tech of UV & EB Formulation for Coatings, Inks & Paints* III 61, 63, 229–232, 280, 405, 1991.

Esrom et al. "Large area Photochemical Dry Etching of Polymers iwth Incoherent Excimer UV Radiation" *MRS Materials Research Society* 1–7 1991.

Esrom et al. Excimer Laser–Induced Decomposition of Aluminum Nitride Material Research Society Fall Meeting 1–6 1991.

Esrom et al. "Metal deposition with a windowless VUV excimer source" *Applied Surface Science* 1–5 1991.

Estrom "Excimer Laser–Induced Surface Activation of Aln for Electroless Metal Deposition" Mat. Res. Sco.lSymp. Proc. 204 457–465 1991.

Zhang et al. "UV–induced decompositin of adsorbed Cu–acetylacetonate films at room temperature for electroless metal plating" *Applied Surface Science* 1–6 1991.

"German company develops reusable paper" *Pulp & Paper* 1991.

Abstract of patent, JP 02289652 1990.

Ohashi et al. "Molecular Mechanics Studies on Inclusion Compounds of Cyanine Dye Monomers and Dimers in Cyclodextrin Cavities," *J. Am. Chem. Soc.* 112 5824–5830 1990.

Kogelschatz et al. "New Incoherent Ultraviolet Excimer Sources for Photolytic Material Deposition," *Laser Und Optoelektronik* 1990.

Patent Abstracts of Japan, JP 02141287 (Dainippon Printing Co Ltd.) May 30, 1990.

Abstract of Patent JP 0297957, (Fuji Xerox Co., Ltd.) 1990.

Derwent Publications Ltd., London, JP 2091166 (Canon KK), Mar. 30, 1990. (Abstract).

Esrom et al. "Metal Deposition with Incoherent Excimer Radiation" Mat. Res. Soc. Symp. Proc. 158 189–198 1990.

Esrom "UV Excimer Laser–Induced Deposition of Palladium from palladiym Acetate Films" Mat. Res. Soc. Symp. Proc. 158 109–117 1990.

Kogelschatz, U. "Silent Discharges for the Generation of ultraviolet and vacuum ultraviolet excimer radiation" *Pure & Applied Chem.* 62 1667–74 1990.

Esrom et al. "Investigation of the mechanism of the UV–induced palladium depostions processf from thin solid palladium acetate films" *Applied Surface Science* 46 158–162 1990.

Zhang et al. "VUV synchrotron radiation processing of thin palladium acetate spin–on films for metallic surface patterning" *Applied Surface Science* 46 153–157 1990.

Brennan et al. "Stereoelectronic effects in ring closure reactions: the 2'-hydroxychalcone—flavanone equilibrium, and related systems," *Canadian J. Chem.* 68 (10) pp. 1780–1785 1990.

Abstract of patent, JP 01–299083 1989.

Derwent Publications Ltd., London, J,O, 1182379 (Canon KK), Jul. 20, 1989. (Abstract).

Derwent Publications Ltd., London, JO 1011171 (Mitsubishi Chem Ind. KK.), Jan. 13, 1989 (Abstract).

Gruber, R.J., et al. "Xerographic Materials" *Encyclopedia of Polymer Science and Engineering* 17 918–943 1989.

Pappas, S.P. "Photocrosslinking" *Comph. Pol. Sci.* 6 135–148 1989.

Pappas, S.P. "Photoinitiated Polymerization" *Comph. Pol. Sci.* 4 337–355 1989.

Kirilenko, G. V. et al. "An analog of the vesicular process with amplitude modulation of the incident light beam" *Chemical Abstracts* 111 569 [No. 111:12363 3b] 1989.

Esrom et al. "UV excimer laser–induced pre–nucleation of surfaces followed by electroless metallization" *Chemtronics* 4 216–223 1989.

Esrom et al. "VUV light–induced depostion of palladium using an incoherent Xe2* excimer source" *Chemtronics* 4 1989.

Esrom et al. "UV Light–Induced Depostion of Copper Films" C5–719–C5–725 1989.

Falbe et al. *Rompp Chemie Lexikon* 9 270 1989.

Allen, Norman S. *Photopolymerisation and Photoimaging Science and Technology* pp. 188–199; 210–239 1989.

Patent Abstracts of Japan, JP 63297477 (Fuji Photo Film Co. Ltd.) Dec. 5, 1988, abstract.

Derwent Publications, Ltd., London, SU 1423656 (Kherson Ind Inst), Sep. 15, 1988 (Abstract).

Derwent Publications, Ltd., London, EP 0280653 (Ciba Geigy AG), Aug. 31, 1988 (Abstract).

Abstract of patent, JP 63–190815 1988.

Patent Abstracts of Japan, JP 63179985 (Tomoegawa Paper Co. Ltd.), Jul. 23, 1988.

Derwent World Patents Index, JP 63179977 (Tomoegawa Paper Mfg Co Ltd), Jul. 23, 1988.

Furcone, S. Y. et al. "Spin–on B14Sr3Ca3Cu4O16+x superconducting thin films from citrate precursors," *Appl. Phys. Lett.* 52(25) 2180–2182 1988.

Abstract of patent JP 63–144329 1988.

Abstract of patent JP 63–130164 1988.

Derwent Publications, Ltd., London, J6 3112770 (Toray Ind Inc). May 17, 1988 (Abstract).

Derwent Publications Ltd., London, J6 3108074 (Konishiroku Photo KK), May 12, 1988 (Abstract).

Derwent Publications Ltd., London,J6 3108073 (Konishiroku Photo KK), May 12, 1988 (Abstract).

Abstract of patent, JP 61–77846 1988.

Abstract of patent, JP 63–73241 1988.

Abstract of patent, JP 63–47762, 1988.

Abstract of patent, JP 63–47763, 1988.

Abstract of patent, JP 63–47764, 1988.

Abstract of patent, JP 63–47765 1988.

Eliasson, B., et al. "UV Excimer Radiation from Dielectric–Barrier Discharges" *Applied Physics B* 46 299–303 1988.

Eliasson et al. "New Trends in High Intensity UV Generation" *EPA Newsletter* (32) 29–40 1988.

Cotton, F.A., "Oxygen: Group Via(16)" *Advanced Inorganic Chemistry* 5th ed. 473–474 1988.

Derwent Publications, Ltd., London, J6 2270665 (Konishiroku Photo KK), Nov. 25, 1987 (Abstract).

Abstract of patent, JP 62–215261 1987.

Derwent World Patents Index JP 62064874 (Dainichiseika Color & Chem Mfg.), Mar. 23, 1987. abstract.

Database WPI, Derwent Publications Ltd., London, JP 62032082 (Mitsubishi Denki KK), Feb. 12, 1987. (Abstract).

Abstract of patent, JP 62–32082 1987.

Derwent Publications Ltd., London, J6 2007772 (ALPS Electric KK.), Jan. 14, 1987 (Abstract).

Gross et al. "Laser direct–write metallization in thin palladium acetate films" *J. App. Phys.* 61 (4) 1628–1632 1987.

Al–Ismail et al. "Some experimental results on thin polypropylene films loaded with finely dispersed copper" *Journal of Materials Science* 415–418 1987.

Baufay et al. "Optical self–regulation during laser–induced oxidation of copper" *J. Appl. Phys* 61 (9) 4640–4651 1987.

Derwent Publications Ltd., London, JA 0284478 (Sanyo Chem Ind Ltd.), Dec. 15, 1986 (Abstract).
Abstract of patent, JP 61251842 1986.
Database WPI, Derwent Publications Ltd., London, GB; SU, A, 1098210 (Kutylya L A) Jun. 23, 1986.
Abstract of patent, JP 61–97025 1986.
Abstract of patent, JP 61–87760 1986.
Derwent Publications Ltd., London, DL 0234731 (Karl Marx Univ. Leipzig), Apr. 9, 1986. (Abstract).
Derwent World Patents Index, SU 1219612 ((AS USSR NON–AQ SOLN) Mar. 23, 1986.
Derwent Publications, Ltd., London, J6 1041381 (Osaka Prefecture), Feb. 27, 1986 (Abstract).
Dialog, JAPIO, JP 61–034057 (Ciba Geigy AG) Feb. 18, 1986.
Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201 1986.
Jellinek, H.H.G. et al. "Evolution of H2O and CO2 During the Copper–Catalyzed Oxidation of Isotactic Polypropylene," *J. Polymer Sci.* 24 389–403 1986.
Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986.
John J. Eisch and Ramiro Sanchez "Selective, Oxophilic Imination of Ketones with Bis (dichloroaluminum) Phenylimide" *J. Org. Chem.* 51 (10) 1848–1852 1986.
Derwent Publications Ltd., London, J6 0226575 (Sumitomo Chem Ind Ltd.), Oct. 11, 1985 (Abstract).
Abstract of patent, JP 60–156761 1985.
Derwent World Patents Index DE 3443565 (Mitsubishi Yuka Fine Che. et al.) Jul. 11, 1985. abstract.
Derwent Publications Ltd., London, J,A, 0011451 (Fugi Photo Film KK), Jan. 21, 1985 (Abstract).
Derwent Publications, Ltd., London J6 0011449–A (Taoka Chemical KK) Jan. 21, 1985 (abstract).
Derwent World Patents Index JP 60–008088 (Mitsubishi Paper Mills Ltd.) Jan. 16, 1985. abstract.
Roos, G. et al. "Textile applications of photocrosslinkable polymers" *Chemical Abstracts* 103 57 [No. 103:23690j] 1985.
Beck, M.T., et al. Mechanism of the autophotosensitized formulation of porphyrins in the reaction of pyrrole and m–disulfonated *Chemical Abstracts* 198 5:45 362 1985.
Derwent World Patents Index, EP 127574 (Ciba Geigy AG), Dec. 5, 1984.
Derwent Publications Ltd., London, JP 0198187 (Canon KK), Nov. 9, 1984. (Abstract).
Derwent Publications Ltd., London, J.A. 0169883 (Ricoh KK), Sep. 25, 1984. (Abstract).
Derwent Publications Ltd., London, JA 0169883 (Ricoh KK), Sep. 25, 1984 (Abstract).
Derwent Publications Ltd., London, JA 0198187 (Canon KK), Nov. 9, 1984 (Abstract).
Derwent Publications Ltd., London, J.A. 0053563 (Dainippon Toryo KK), Mar. 28, 1984. (Abstract).
Derwent Publications Ltd., London, J.A. 0053562 (Dainippon Toryo KK), Mar. 28, 1984. (Abstract).
Abstract of Patent, JA 0053563 (Dainippon Toryo KK), Mar. 28, 1984 (Abstract).
Abstract of Patent, JA 0053562 (Dainippon Toryo KK), Mar. 28, 1984 (Abstract).

Derwent Publications Ltd., London, J.A. 0051961 (Dainippon Toryo KK), Mar. 26, 1984). (Abstract).
Abstract of Patent, JA 0051961 (Dainippon Toryo KK), Mar. 26, 1984 (Abstract).
Saenger, W. "Structural Aspects of Cyclodextrins and Their Inclusion Complexes" *Inclusion Compounds—Structural Aspects of Inclusion Compounds formed by Organic Host* 2 231–259 1984.
Szejtli "Industrial Applications of Cyclodextrins" *Inclusion Compounds: Physical Prop. & Applns* 3 331–390 1984.
Kano et al. "Three–Component Complexes of Cyclodextrins. Exciplex Formation in Cyclodextrin Cavity," *J. Inclusion Phenomena* 2 pp. 715–724 1984.
Suzuki et al. "Spectroscopic Investigation of Cyclodextrin Monomers, Derivatives, Polymers and Azo Dyes," *J. Inclusion Phenomena* 2, pp. 715–724 1984.
Abstract of Patent, JA 0222164 (Ricoh KK), Dec. 23, 1983 (Abstract).
Abstract of patent, JP 58211426 (Sekisui Plastics KK), Dec. 8, 1983.
Derwent Publications Ltd., London, EP 0072775 (Ciba Geigy AG), Feb. 23, 1983 (Abstract).
van Beek, H.C.A "Light–Induced Colour Changes in Dyes and Materials" *Color Res. and Appl.* 8 176–181 1983.
Connors, K.A. "Applications of a stoichiometric model of cyclodextrin complex formation" *Chemical Abstracts* 98 598 [No. 98:53067g] 1983.
Abstract of Patent, EP 0065617 (IBM Corp.), Dec. 1, 1982 (Abstract).
Derwent Publications Ltd., London, J.A. 0187289 (Honshu Paper Mfg KK), Nov. 17, 1982. (Abstract).
Abstract of Patent, JA 0187289 (Abstract).
Abstract of Patent, JA 0185364 (Ricoh KK), Nov. 15, 1982 (Abstract).
Derwent Publications, Ltd., London J5 7139146 (Showa Kako KK) Aug. 27, 1982 (abstract).
Abstract of Patent, JA 0090069 (Canon KK), Jun. 4, 1982 (Abstract).
Derwent Publications, Ltd., London, JA 0061785 (Nippon Senka KK), Apr. 14, 1982 (Abstract).
Fischer, "Submicroscopic contact imaging with visible light by energy transfer" *Appl. Phys. Letter* 40(3) 1982.
Abstract of Patent, JA 0010659 (Canon KK), Jan. 20, 1982 (Abstract).
Abstract of Patent, JA 0010661 (Canon KK), Jan. 20, 1982 (Abstract).
Christen "Carbonylverbindungen: Aldehyde und Ketone," *Grundlagen der Organischen Chemie* 255 1982.
Derwent Publications Ltd., London, J.A. 0155263 (Canon KK), Dec. 1, 1981. (Abstract).
Abstract of Patent, JA 0155263 (Canon KK), Dec. 1, 1981 (Abstract).
Abstract of Patent, JA 0147861 (Canon KK), Nov. 17, 1981. (Abstract).
Derwent Publications Ltd., London, J.A. 0143273 (Canon KK), Nov. 7, 1981. (Abstract).
Abstract of Patent, JP 56143272 (Canon KK), Nov. 7, 1981 (Abstract).
Patent Abstracts of Japan, JP 56143274 (Canon Inc.) Nov. 7, 1981, abstract.
Abstract of Patent, JA 0136861 (Canon KK), Oct. 26, 1981 (Abstract).
Abstract of Patent, JA 6133378 (Canon KK), Oct. 19, 1981 (Abstract).

Abstract of Patent, JA 6133377 (Canon KK), Oct. 19, 1981 (Abstract).
Abstract of Patent, JA 6093775 (Canon KK), Jul. 29, 1981 (Abstract).
Derwent Publications Ltd., London, J.A. 0008135 (Ricoh KK), Jan. 27, 1981. (Abstract).
Derwent Publication Ltd., London, J.A. 0004488 (Canon KK), Jan. 17, 1981. (Abstract).
Abstract of Patent, JA 0004488 (Canon KK), Jan. 17, 1981 (Abstract).
Kirk–Othmer "Metallic Coatings," *Encyclopedia of Chemical Technology* 15 241–274 1981.
Komiyama et al. "One–Pot Preparation of 4–Hydroxychalcone β–Cyclodextrin as Catalyst," *Makromol. Chem.* 2 733–734 1981.
Derwent Publications, Ltd., London CA 1086–719 (Sherwood Medical) Sep. 30, 1980 (abstract).
Derwent Publications Ltd., Database WPI, JP 55 113036 (Ricoh KK), Sep. 1, 1980.
Rosanske et al. "Stoichiometric Model of Cyclodextrin Complex Formation" *Journal of Pharmaceutical Sciences* 69 (5) 564–567 1980.
Semple et al. "Synthesis of Functionalized Tetrahydrofurans," *Tetrahedron Letters* 81 pp. 4561–4564 1980.
Kirk–Othmer "Film Deposition Techniques," *Encyclopedia of Chemical Technology* 10 247–283 1980.
Derwent World Patents Index, Derwent Info. Ltd., JP 54158941 (Toyo Pulp KK), Dec. 15, 1979. (Abstract).
Derwent World Patents Index, JP 54117536 (Kawashima F) Sep. 12, 1979.
Derwent Publications, Ltd., London, J.A. 0005422 (Fuji Photo Film KK), Jan. 16, 1979. (Abstract).
Drexhage et al. "Photo–bleachable dyes and processes" Research Disclosure 85–87 1979.
"Color imaging devices and color filter arrays using photo–bleachable dyes" Research Disclosure 22–23 1979.
Wolff, N.E., et al. "Electrophotography" *Kirk–Othmer Encyclopedia of Chemical Technology* 8 794–826 1979.
Derwent Publications Ltd., London, J.A. 0012037 (Pentel KK), Jan. 29, 1977. (Abstract).
Abstract of Patent, JA 0012037 (Pentel KK), Jan. 29, 1977 (Abstract).
Jenkins, P. W. et al. "Photobleachable dye material" Research Disclosure 18 [No. 12932] 1975.
Lamberts, R.L. "Recording color grid patterns with lenticules" *Research Disclosure* 18–19 [No. 12923] 1975.
Karmanova, L.S. et al. "Light stabilizers of daytime fluorescent paints" *Chemical Abstracts* 82 147 [No. 59971p] 1975.
Prokopovich, B. et al. "Selection of effective photoinducers for rapid hardening of polyester varnish PE–250" *Chemical Abstracts* 83 131 [No. 81334a] 1975.
"Variable Contrast Printing System" Research Disclosure 19 [No. 12931] 1975.

Lakshman "Electronic Absorption Spectrum of Copper Formate Tetrahydrate" *Chemical Physics Letters* 31 (2) 331–334 1975.
Derwent Publications, Ltd., London J4 9131–226 (TNational Cash Register C) Dec. 16, 1974 (abstract).
Chang, I.F., et al. "Color Modulated Dye Ink Jet Printer" IBM Technical Disclosure Bulletin 17(5) 1520–1521 1974.
"Darocur 1173: Liquid Photoiniator for Ultraviolet Curing of Coatings" 1974.
Hosokawa et al. "Ascofuranone, an antibiotic from Ascochyta," Japan Kokai 73 91,278 (Nov. 28, 1973) *Merck Index* 80 p. 283; abstract 94259t 1974.
Abstract of patent, NL 7112489 (Dec. 27, 1971).
Gafney et al. "Photochemical Reactions of Copper (II)—1, 3–Diketonate Complexes" *Journal of the Americqal Chemical Society* 1971.
Derwent Publications, Ltd., London SU 292698–S Jan. 15, 1971 (abstract).
Derwent World Patents Index,CS 120380 (Kocourek, Jan) Oct. 15, 1966.
Tsuda et al. Vinyl Polymerization. CXLVI. The influence of dibenzoyl disulfide derivatives on radical polymerizations *Chemical Abstract* 196 6:29 198 1966.
Rigdon, J.E. "In Search of Paper that Spies Can't Copy" *Wall Street Journal*.
Chatterjee,S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338.
"Assay—Physical and Chemical Analysis of Complexes AMAIZO. Analysis of Complexes".
"Cyclodextrin" AMAIZO.
"Beta Cyclodextrin Polymer (BCDP)" AMAIZO.
"Chemically Modified Cyclodextrins" AMAIZO.
"Cyclodextrin Complexation" American Maize Products Co.
"Monomers" Scientific Polymers Products Inc.
Suppan, Paul "Quenching of Excited States" *Chemistry and Light* 65–69.
Yamaguchi, H. et al. "Supersensitization. Aromatic ketones a supersensitizers" *Chemical Abstracts* 53 107 (d).
Stecher, H. "Ultraviolet–adsorptive additives in adhesives, lacquers and plastics" *Chemical Abstracts* 53 14579 (c).
Maslennikov, A.S. "Coupling of diazonium salts with ketones" *Chemical Abstracts* 60 3128e.
Derwent Publications Ltd., London, 4 9128022.
Abstract of Patent, JP 405195450.
Rose, Philip I. "Gelatin," *Encyclopedia of Chemical Technology* 7 488–513.

* cited by examiner

PHOTOINITIATORS AND APPLICATIONS THEREFOR

This Application claims priority under 35 USC §119(e) of U.S. provisional patent application Ser. No. 60/087,866, filed Jun. 03, 1998.

TECHNICAL FIELD

The present invention relates to novel photoinitiators and methods for generating a reactive species using the photoinitiators. The present invention further relates to methods of polymerizing or photocuring polymerizable unsaturated material using the above-mentioned photoinitiators.

BACKGROUND OF THE INVENTION

Polymers have served essential needs in society. For many years, these needs were filled by natural polymers. More recently, synthetic polymers have played an increasingly greater role, particularly since the beginning of the 20th. century. Especially useful polymers are those prepared by an addition polymerization mechanism, i.e., free radical chain polymerization of unsaturated monomers, and include, by way of example only, coatings and adhesives. In fact, the majority of commercially significant processes is based on free-radical chemistry. That is, chain polymerization is initiated by a reactive species, which often is a free radical. The source of the free radicals is termed an initiator or photoinitiator.

Improvements in free radical chain polymerization have focused both on the polymer being produced and the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate, which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by either of two pathways:

(1) the photoinitiator undergoes excitation by energy absorption with subsequent decomposition into one or more radicals; or (2) the photoinitiator undergoes excitation and the excited species interacts with a second compound (by either energy transfer or a redox reaction) to form free radicals from the latter and/or former compound(s).

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, commercially available radiation sources, such as medium and high-pressure mercury and xenon lamps, emit over a wide wavelength range, thus producing individual emission bands of relatively low intensity. Most photoinitiators only absorb over a small portion of the emission spectra and, as a consequence, most of the lamps' radiation remains unused.

In addition, most known photoinitiators have only moderate "quantum yields" (generally less than 0.4) at these wavelengths, indicating that the conversion of light radiation to radical formation can be more efficient.

Thus, there are continuing opportunities for improvements in free radical polymerization photoinitiators. Moreover, there is a need in the art for new, energy-efficient photoinitiators for use in a variety of polymerization and photocuring processes.

SUMMARY OF THE INVENTION

The present invention addresses some of the difficulties and problems discussed above by the discovery of energy-efficient photoinitiators having the following general formula:

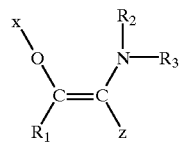

wherein $R_1$, $R_2$ and $R_3$ each independently represent H—, an alkyl group, a chalcone, phthaloylglycine, $HSO_3$—, $NaSO_3$—,

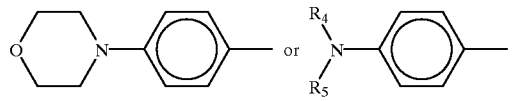

vinyl thioether,
wherein $R_4$ and $R_5$ each independent represent an alkyl

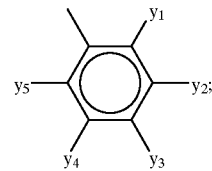

Z group; x represents an alkyl group or represents an alkyl group, an alkylaryl group or

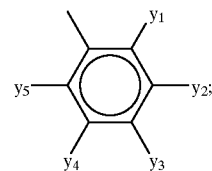

wherein $y_1$, $y_2$, $y_3$, $y_4$ and $y_5$ each independently represent H—, $HSO_3$—, $NaSO_3$—, HOOC—, NaOOC— and alkyl group. By selecting particular "R" groups or "antennae," wavelength selective photoinitiators are produced having a desired absorption maximum varying from about 222 nm to about 390 nm. Further, by selecting one or more ionic substituents, $y_1$, $y_2$, $y_3$, $y_4$ or $y_5$, water-soluble photoinitiators are produced.

The present is directed to the above-described α-amine enol ether photoinitiators, compositions containing the same, and methods for generating a reactive species which included providing one or more of the photoinitiators and irradiating the one or more photoinitiators. One of the main advantages of the photoinitiators of the present invention is that they efficiently generate one or more reactive species under extremely low energy lamps, such as excimer lamps and mercury lamps, as compared to prior art photoinitiators. Further, the photoinitiators of the present invention are as much as five times faster that the best prior art photoinitiators.

The present invention is further directed to methods of using the above-described α-amine enol ether photoinitiators to polymerize and/or photocure a polymerizable material. The photoinitiators of the present invention result in rapid curing times in comparison to the curing times of prior art photoinitiators, even with relatively low output lamps. The present invention includes a method of polymerizing an unsaturated monomer by exposing the unsaturated monomer to radiation in the presence of the efficacious wavelength specific photoinitiator composition described above. When an unsaturated oligomer/monomer mixture is employed in place of the unsaturated monomer, curing is accomplished.

The present invention further includes a film and a method for producing a film, by drawing an admixture of unsaturated polymerizable material and one or more α-amine enol ether photoinitiators of the present invention, into a film and irradiating the film with an amount of radiation sufficient to polymerize the composition. The admixture may be drawn into a film on a nonwoven web or on a fiber, thereby providing a polymer-coated nonwoven web or fiber, and a method for producing the same.

The present invention is also directed to an adhesive composition comprising an unsaturated polymerizable material admixed with one or more α-amine enol ether photoinitiators of the present invention. Similarly, the present invention includes a laminated structure comprising at least two layers bonded together with the above-described adhesive composition, in which at least one layer is a nonwoven web or film. Accordingly, the present invention provides a method of laminating a structure wherein a structure having at least two layers with the above-described adhesive composition between the layers is irradiated to polymerize the adhesive composition.

These and other features and advantages of the present invention will become apparent after a review of the following detailed description of the disclosed embodiments and the appended claims.

DETAILED DESCRIPTION OF THE INVENTION

The present invention is directed to energy-efficient, reactive, α-amine enol ether photoinitiators and methods for utilizing the same. More particularly, the present invention is directed to new photoinitiators having the following general formula:

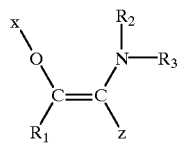

wherein $R_1$, $R_2$ and $R_3$ each independently represent H—, an alkyl group, a chalcone, phthaloylglycine, $HSO_3$—, $NaSO_3$—, vinyl thioether,

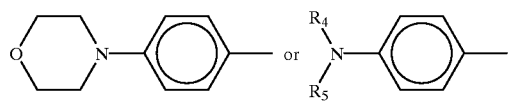

wherein $R_4$ and $R_5$ each independently represent an alkyl group; x represents an alkyl group or

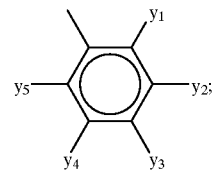

z represents an alkyl group, an alkylaryl group or

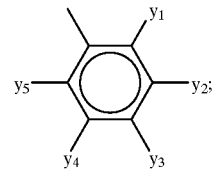

wherein $y_1$, $y_2$, $y_3$, $y_4$ and $y_5$ each independently represent H—, $HSO_3$—, $NaSO_3$—, HOOC—, NaOOC — and an alkyl group.

The present invention also includes a method of polymerizing an unsaturated polymerizable material by exposing the unsaturated material to radiation in the presence of one or more of the α-amine enol ether photoinitiators described above. Further, the present invention is directed to a film and a method for producing a film, by drawing an admixture of unsaturated polymerizable material and one or more of the α-amine enol ether photoinitiators described above, into a film and irradiating the film with an amount of radiation sufficient to polymerize the admixture.

The present invention is further directed to an adhesive composition comprising an unsaturated polymerizable material admixed and one or more α-amine enol ether photoinitiators of the present invention. Similarly, the present invention includes a laminated structure comprising at least two layers bonded together with the above-described adhesive composition. The present invention further provides a method of laminating a structure wherein a structure having at least two layers with the above-described adhesive composition between the layers is irradiated to polymerize the adhesive composition.

After the following definitions, the photoinitiators of the present invention will be described in detail, followed by a detailed description of the method of generating reactive species, and the various representative applications of the method.

Definitions

As used herein, the term "reactive species" is used herein to mean any chemically reactive species including, but not limited to, free-radicals, cations, anions, nitrenes, and carbenes. Illustrated below are examples of several of such species. Examples of carbenes include, for example, methylene or carbene, dichlorocarbene, diphenylcarbene, alkylcarbonylcarbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, primary, secondary, and tertiary alkyl carbocations, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, n-propyl anion, isobutyl anion, and neopentyl anion; cycloalkyl anions, such as cyclopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diaryltitanocenes, iron arene complexes, manganese decacarbonyl, and methylcyclopentadienyl manganese tricarbonyl. Organometallic photoinitiators generally produce free radicals or cations.

As used herein, the term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

As used herein, the term "polymerization" is used herein to mean the combining, e.g. covalent bonding, of large numbers of smaller molecules, such as monomers, to form very large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a cross-linked polymer network. Thus, curing is the polymerization of unsaturated monomers or oligomers in the presence of cross-linking agents.

As used herein, the terms "unsaturated monomer," "functional oligomer," and "cross-linking agent" are used herein with their usual meanings and are well understood by those having ordinary skill in the art. The singular form of each is intended to include both the singular and the plural, i.e., one or more of each respective material.

As used herein, the term "unsaturated polymerizable material" is meant to include any unsaturated material capable of undergoing polymerization. The term encompasses unsaturated monomers, oligomers, and cross-linking agents. Again, the singular form of the term is intended to include both the singular and the plural.

As used herein, the term "fiber" as used herein denotes a threadlike structure. The fibers used in the present invention may be any fibers known in the art. As used herein, the term "nonwoven web" as used herein denotes a web-like matter comprised of one or more overlapping or interconnected fibers in a nonwoven manner. It is to be understood that any nonwoven fibers known in the art may be used in the present invention.

Photoinitiators

The present invention is directed to new α-amine enol ether photoinitiators having the following general formula:

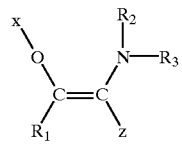

wherein $R_1$, $R_2$ and $R_3$ each independently represent H—, an alkyl group, a chalcone, phthaloylglycine, $HSO_3$—, $NaSO_3$—, vinyl thioether,

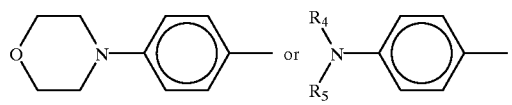

wherein $R_4$ and $R_5$ each independently represent an alkyl group; x represents an alkyl group or

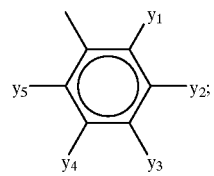

z represents an alkyl group, an alkylaryl group or

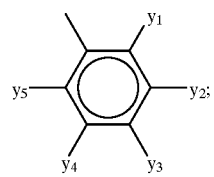

wherein $y_1$, $y_2$, $y_3$, $y_4$ and $y_5$ each independently represent H—, $HSO_3$—, $NaSO_3$—, HOOC—, NaOOC — and an alkyl group. By selecting particular "R" groups or "antennae," wavelength selective photoinitiators are produced having a desired absorption maximum varying from about 222 nm to about 390 nm. As used herein, the term "antennae" refers to a moiety on the α-amine enol ether photoinitiators of the present invention, which absorbs radiation from a radiation source and transfers the absorbed energy to an excitable portion of the photoinitiator molecule. Further, by selecting one or more ionic substituents, $y_1$, $y_2$, $y_3$, $y_4$ or $y_5$, water-soluble photoinitiators may be produced.

In one embodiment of the present invention, the α-amine enol ether photoinitiator comprises a compound having the following formula:

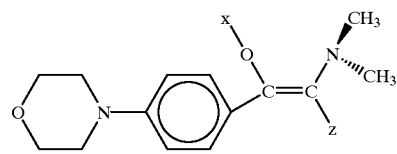

wherein x and z are as defined above. This particular photoinitiator contains a single morpholino group ("antenna") and has an absorption maximum at about 360 nm. In a further embodiment of the present invention, the α-amine enol ether photoinitiator comprises a compound having the following formula:

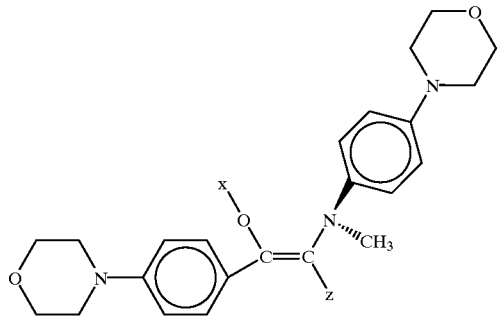

wherein x and z are as defined above. By adding a second morpholino group to the photoinitiator, the absorption maximum of the photoinitiator shifts to about 380 nm. In yet a further embodiment of the present invention, the photoinitiator comprises a compound having the following formula:

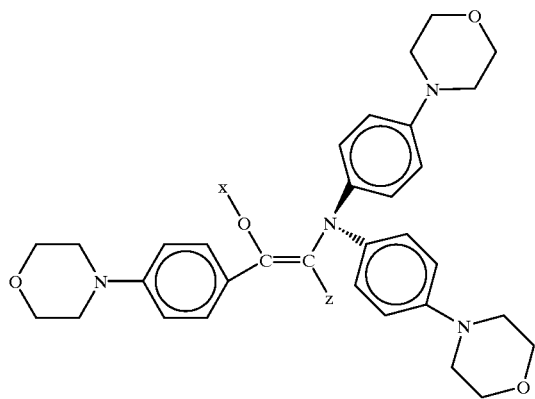

wherein x and z are as defined above. By adding a third morpholino group to the photoinitiator, the absorption maximum of the photoinitiator shifts to about 390 nm.

In yet another embodiment of the present invention, the photoinitiator comprises a water-soluble photoinitiator having the following structure:

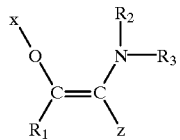

wherein $R_1$, $R_2$ and $R_3$ each independently represent H—, an alkyl group, a chalcone, phthaloylglycine, $HSO_3$—, $NaSO_3$—, vinyl thioether,

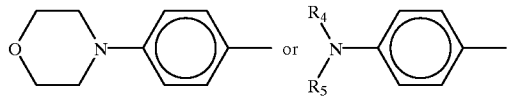

wherein $R_4$ and $R_5$ each independently represent an alkyl group; x represents an alkyl group or

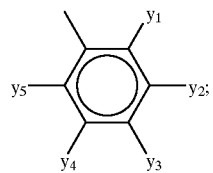

z represents an alkyl group, an alkylaryl group or

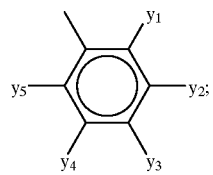

wherein at least one of $y_1$, $y_2$, $y_3$, $y_4$ and $y_5$ represents $NaSO_3$— or NaOOC—.

In a further embodiment of the present invention, the photoinitiator comprises an α-amino enol ether compound containing a phthaloylglycine antennae and having the following formula:

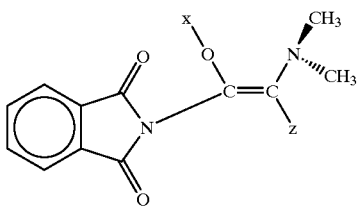

wherein x and z are as defined above. This particular photoinitiator contains a phthaloylglycine group ("antenna") and has an absorption maximum at 222 nm.

In yet a further embodiment of the present invention, the photoinitiator comprises an α-amino enol ether compound containing a 2,2-diphenylvinyl phenyl sulfide antennae and having the following formula:

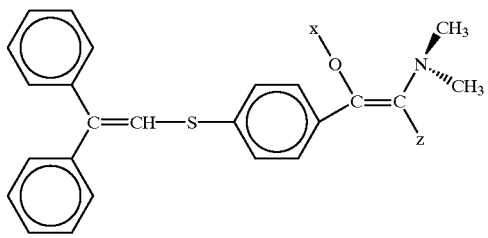

wherein x and z are as defined above. This particular photoinitiator has an absorption maximum at 308 nm.

The α-amino enol ether photoinitiators of the present invention may be prepared by any reaction mechanism known to those of ordinary skill in the art as long as the α-amino enol ether structure remains intact.

The resulting α-amino enol ether photoinitiators are relatively stable at room temperature (from about 15° C. to 25° C.) and normal room humidity (from about 30% to 60%). However, upon exposure to radiation at an appropriate wavelength, the photoinitiators efficiently produce one or more free radicals. The α-amino enol ether photoinitiators of the present invention have a high intensity of absorption. For example, the photoinitiators of the present invention may have a molar extinction coefficient greater than about 5,000 liters per mole per cm (1 mole$^{-1}$cm$^{-1}$) at an absorption maximum.

As another example, the photoinitiators of the present invention may have a molar extinction coefficient (absorptivity) greater than about 10,000 1 mole$^{-1}$cm$^{-1}$. As another example, the photoinitiators of the present invention may have a molar extinction coefficient (absorptivity) greater than about 20,000 1 mole$^{-1}$cm$^{-1}$. As a further example, the photoinitiators of the present invention will have a molar extinction coefficient greater than about 25,000 1 mole$^{-1}$cm$^{-1}$.

Method of Generating a Reactive Species and Applications Therefor

The present invention is also directed to a method of generating a reactive species. The method of generating a reactive species involves generating a reactive species by exposing one or more of the above-described α-amino enol ether photoinitiators to radiation. The exposure of the photoinitiators to a radiation source triggers a photochemical process. As stated above, the term "quantum yield" is used herein to indicate the efficiency of a photochemical process. More particularly, quantum yield is a measure of the probability that a particular molecule (photoinitiator) will absorb a quantum of light during its interaction with a photon. The term expresses the number of photochemical events per photon absorbed. Thus, quantum yields may vary from zero (no absorption) to 1.

The α-amino enol ether photoinitiators of the present invention absorb photons having a specific wavelength and transfers the absorbed energy to one or more excitable portions of the molecule. The excitable portion of the molecule absorbs enough energy to cause a bond breakage, which generates one or more reactive species. The efficiency with which a reactive species is generated with the photoinitiators of the present invention is significantly greater than that experienced with photoinitiators of the prior art as indicated by faster cure times. For example, the α-amino enol ether photoinitiators of the present invention desirably will have a quantum yield greater than about 0.5. More desirably, the quantum yield of the photoinitiators of the present invention will be greater than about 0.6. Even more desirably, the quantum yield of the photoinitiators of the present invention will be greater than about 0.7. Still more desirably, the quantum yield of the photoinitiators of the present invention will be greater than about 0.8, with the most desirable quantum yield being greater than about 0.9.

Exposing the α-amino enol ether photoinitiators of the present invention to radiation results in the generation of one or more reactive species. Thus, the photoinitiators may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene, propylene, vinyl chloride, isobutylene, styrene, isoprene, acrylonitrile, acrylic acid, methacylic acid, ethyl acrylate, methyl methacrylate, vinyl acrylate, allyl methacrylate, tripropylene glycol diacrylate, trimethylol propane ethoxylate acrylate, epoxy acrylates, such as the reaction product of a bisphenol A epoxide with acrylic acid; polyether acrylates, such as the reaction product of acrylic acid with an adipic acid/hexanediol-based polyether, urethane acrylates, such as the reaction product of hydroxypropyl acrylate with diphenylmethane-4,4'-diisocyanate, and polybutadiene diacrylate oligomer.

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

Accordingly, the present invention also comprehends a method of polymerizing an unsaturated monomer by exposing the unsaturated monomer to radiation in the presence of the efficacious α-amino enol ether photoinitiators of the present invention described above. When an unsaturated oligomer/monomer mixture is employed in place of the unsaturated monomer, curing is accomplished. It is to be understood that the polymerizable material admixed with the α-amino enol ether photoinitiators of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of photoinitiators, the identity and amount of the polymerizable material, the intensity and wavelength of the radiation, and the duration of exposure to the radiation.

It is believed that radiation exposure results in the generation of free radicals from the α-amino enol ether photoinitiators of the present invention by one or more of the following: cleavage of a the oxygen-carbon bond resulting in an alkoxy radical; and breakdown of the ether radical to form one or more radicals.

Polymer Films, Coated Fibers and Webs, and Adhesive Compositions

The present invention further includes a film and a method for producing a film, by drawing an admixture of unsaturated polymerizable material and one or more α-amino enol ether photoinitiators of the present invention, into a film and irradiating the film with an amount of radiation sufficient to polymerize the composition. When the unsaturated polymerizable material is an unsaturated oligomer/monomer mixture, curing is accomplished. Any film thickness may be produced, as per the thickness of the admixture formed, so long as the admixture sufficiently polymerizes upon exposure to radiation. The admixture may be drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of photoinitiator, the identity and amount of the polymerizable material, the thickness of the admixture, the intensity and wavelength of the radiation, and duration of exposure to the radiation.

The present invention also includes an adhesive composition comprising an unsaturated polymerizable material admixed with one or more α-amino enol ether photoinitiators of the present invention. Similarly, the present invention includes a laminated structure comprising at least two layers bonded together with the above-described adhesive composition. In one embodiment of the present invention, a laminate is produced wherein at least one layer is a cellulosic or polyolefin nonwoven web or film. Accordingly, the present invention provides a method of laminating a structure wherein a structure having at least two layers with the above-described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the laminates of the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of photoinitiator, the identity and amount of the polymerizable material, the thickness of the admixture, the identity and thickness of the layer, the intensity and wavelength of the radiation, and the duration of exposure to the radiation.

The radiation to which the $\alpha$-amino enol ether photoinitiators of the present invention may be exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers. Desirably, the radiation will be ultraviolet radiation having a wavelength of from about 4 to about 400 nanometers. More desirably, the radiation will have a wavelength of from about 100 to about 390 nanometers, and even more desirably will have a wavelength of from 200 to about 390 nanometers. For example, the radiation may have a wavelength of from about 222 to about 390 nanometers. The radiation desirably will be incoherent, pulsed ultraviolet radiation from a dielectric barrier discharge excimer lamp or radiation from a mercury lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent discharges for the generation of ultraviolet and vacuum ultraviolet excimer radiation." Pure & Appl. Chem., 62, No. 9, pp. 16671674 (1990); and E. Eliasson and U. Kogelschatz, "UV Excimer Radiation from Dielectric- Barrier Discharges." Appl. Phys. B. 46, pp. 299–303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

The source of radiation used with the $\alpha$-amino enol ether photoinitiators of the present invention may be any radiation source known to those of ordinary skill in the art. In one embodiment of the present invention, a mercury lamp with a D-bulb, which produces radiation having an emission peak of 350 nm is used to produce free radicals from the above-described photoinitiators. This radiation source is particularly useful when matched with one or more photoinitiators of the present invention having an absorption maximum of 350 nanometers, corresponding to the emission peak of the mercury lamp. Other specialty doped lamps, which emit radiation at about 390 nm, may be used with photoinitiators of the present invention which have an absorption maximum at 390 nm.

As a result of the $\alpha$-amino enol ether photoinitiators of the present invention absorbing radiation in the range of about 250 to about 390 nanometers, some of the photoinitiators of the present invention will generate one or more reactive species upon exposure to sunlight. Accordingly, these photoinitiators of the present invention provides a method for the generation of reactive species that does not require the presence of a special light source.

The $\alpha$-amino enol ether photoinitiators of the present invention enable the production of adhesive and coating compositions that consumers can apply to a desired object and polymerize or cure upon exposure to sunlight. These photoinitiators also enable numerous industry applications wherein unsaturated polymerizable materials may be polymerized merely upon exposure to sunlight. Therefore, depending upon how the photoinitiator is designed, the photoinitiator of the present invention can eliminate the cost of purchasing and maintaining light sources in numerous industries wherein such light sources are necessary without the photoinitiators of the present invention.

The effective tuning of the $\alpha$-amino enol ether photoinitiators of the present invention for a specific wavelength band permits the photoinitiators of the present invention to more efficiently utilize the target radiation in the emission spectrum of the radiating source corresponding to the "tuned" wavelength band, even though the intensity of such radiation may be much lower than, for example, radiation from a narrow band emitter, such as an excimer lamp. For example, it may be desirable to utilize an excimer lamp, or other radiation emission source, that emits radiation having a wavelength of approximately 222 nm with the phthaloylglycine-containing photoinitiators of the present invention. Similarly, it may be desirable to utilize a mercury lamp that emits radiation having a wavelength of approximately 325 nm, 360 nm or 390 nm with the single, double or triple morpholino-containing photoinitiators of the present invention. However, the effectiveness of the photoinitiators of the present invention is not necessarily dependent upon the availability or use of a narrow wavelength band radiation source.

Accordingly, a major advantage of the α-amino enol ether photoinitiators of the present invention is that they have rapid curing times in comparison to the curing times of prior art photoinitiators. The α-amino enol ether photoinitiators of the present invention possess rapid curing times from 3–5 times faster than the curing times of the best known photoinitiators. Another advantage of the present invention is that the α-amino enol ether photoinitiators of the present invention are highly sensitive photoinitiators and are beneficially used in situations having lower light levels.

Although specific antennae are disclosed above in combination with the photoinitiators of the present invention, it should be understood that any antennae may be used with the α-amino enol ether photoinitiators of the present invention.

The present invention is further described by the examples which follow. Such examples, however, are not to be construed as limiting in any way either the spirit or the scope of the present invention. In the examples, all parts are by weight, unless stated otherwise.

Comparative Example 1

Photocuring of CGI 369 in Red Flexo Resin

A mixture of Ciba Geigy photoinitiator 369 (CGI 369) in the form of a powder was added to a 1 g sample of red flexo ink (Gamma Graphics). The mixture was exposed to UV radiation while positioned within an FTIR machine to monitor the decrease in carbon-carbon double bonds within the mixture. The curing rate was measured.

EXAMPLE 1

Photocuring of KCI 993 in Red Flexo Resin

A mixture of Kimberly Clark's KCI 993 photoinitiator, having the following structure, in the form of a powder was added to a 1 g sample of red flexo ink (Gamma Graphics).

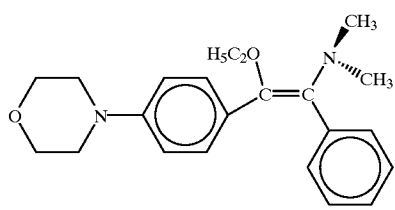

The mixture was exposed to UV radiation while positioned within an FTIR machine to monitor the decrease in carbon-carbon double bonds within the mixture. The curing rate was measured. The KCI 993 photoinitiator had a curing rate relative to the CGI 369 photoinitiator of greater than 220%.

Comparative Example 2

Photocuring of CGI 369 in Blue Flexo Resin

A mixture of CGI 369 in the form of a powder was added to a 1 g sample of blue flexo ink (Gamma Graphics). The mixture was exposed to UV radiation while positioned within an FTIR machine to monitor the decrease in carbon-carbon double bonds within the mixture. The curing rate was measured.

EXAMPLE 2

Photocuring of KCI 993 in Blue Flexo Resin

A mixture of KCI 993 photoinitiator in the form of a powder was added to a 1 g sample of blue flexo ink (Gamma Graphics). The mixture was exposed to UV radiation while positioned within an FTIR machine to monitor the decrease in carbon-carbon double bonds within the mixture. The curing rate was measured. The KCI 993 photoinitiator had a curing rate relative to the CGI 369 photoinitiator of greater than 360%.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A photoinitiator having the following formula:

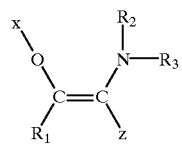

wherein $R_1$, $R_2$ and $R_3$ each independently represent H—, an alkyl group, a chalcone, phthaloylglycine, $HSO_3$—, $NaSO_3$—, vinyl thioether,

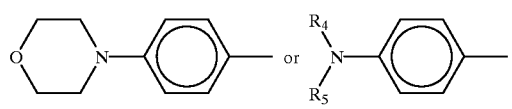

wherein $R_4$ and $R_5$ each independently represent an alkyl group; x represents an alkyl group or

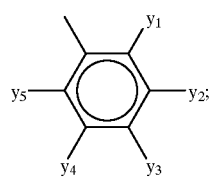

z represents an alkyl group, an alkylaryl group or

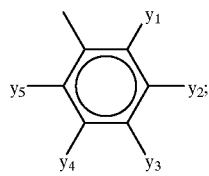

wherein $y_1$, $y_2$, $y_3$, $y_4$ and $y_5$ each independently represent H—, $HSO_3$—, $NaSO_3$—, HOOC—, NaOOC— and an alkyl group.

2. The photoinitiator of claim 1, wherein the photoinitiator has the following structure:

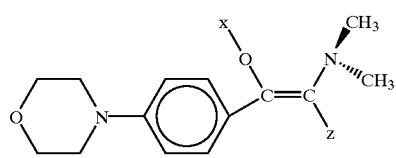

3. The photoinitiator of claim 2, wherein the photoinitiator has the following structure:

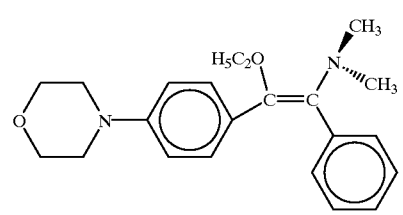

4. The photoinitiator of claim 1, wherein the photoinitiator has the following structure:

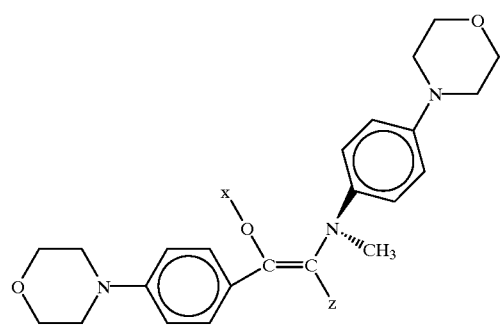

5. The photoinitiator of claim 4, wherein the photoinitiator has the following structure:

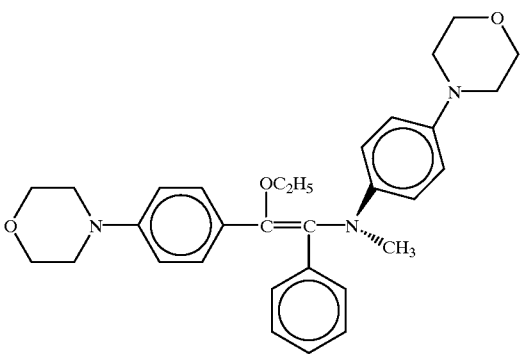

6. The photoinitiator of claim 1, wherein the photoinitiator has the following structure:

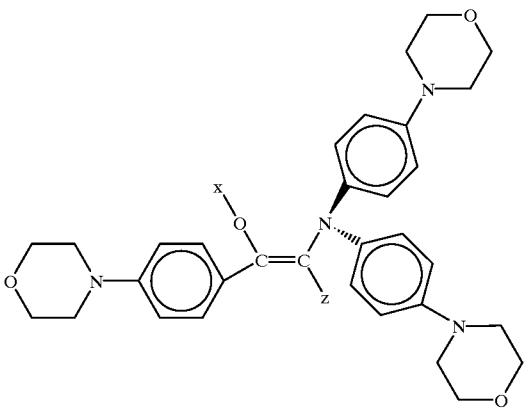

7. The photoinitiator of claim 6, wherein the photoinitiator has the following structure:

8. The photoinitiator of claim 1, wherein the photoinitiator has the following structure:

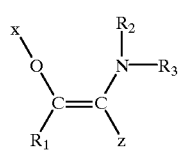

wherein $R_1$, $R_2$ and $R_3$ each independently represent H—, an alkyl group, a chalcone, phthaloylglycine, $HSO_3$—, $NaSO_3$—, vinyl thioether,

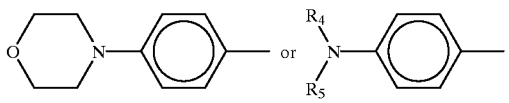

wherein $R_4$ and $R_5$ each independently represent an alkyl

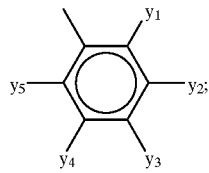

z group; x represents an alkyl group or represents an alkyl group, an alkylaryl group or

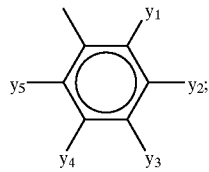

wherein $y_1$, $y_2$, $y_3$, $y_4$ and $y_5$ each independently represent H—, $HSO_3$—, $NaSO_3$—, HOOC—, NaOOC— and an alkyl group; and wherein at least one of $y_1$, $y_2$, $y_3$, $y_4$ and $y_5$ represents $NaSO_3$— or NaOOC—.

9. The photoinitiator of claim 1, wherein the photoinitiator has the following structure:

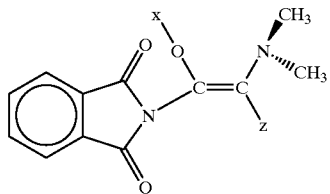

10. The photoinitiator of claim 9, wherein the photoinitiator has the following structure:

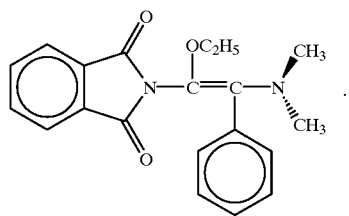

11. The photoinitiator of claim 1, wherein the photoinitiator has the following structure:

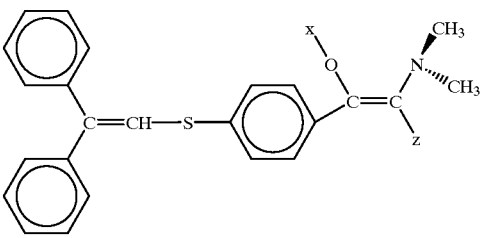

12. The photoinitiator of claim 11, wherein the photoinitiator has the following structure:

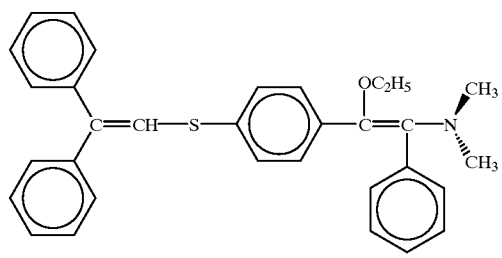

13. A method of generating a reactive species, comprising
irradiating the photoinitiator of claim 1 with radiation.

14. A method of polymerizing an unsaturated polymerizable material, comprising irradiating an admixture of an unsaturated polymerizable material and the photoinitiator of claim 1.

15. A polymer film, produced by the process of:
providing an admixture of an unsaturated polymerizable material and the photoinitiator of claim 1 that has been drawn into a film; and
irradiating the film with an amount of radiation sufficient to polymerize the admixture.

16. A method of coating a nonwoven web comprising:
providing a nonwoven web coated with an admixture of unsaturated polymerizable material and the photoinitiator of claim 1; and
irradiating the coating on the web with an amount of radiation sufficient to polymerize the admixture.

17. A method of coating a fiber comprising:
providing a fiber coated with an admixture of unsaturated polymerizable material and the photoinitiator of claim 1; and
irradiating the coating on the fiber with an amount of radiation sufficient to polymerize the admixture.

18. A method of making a wavelength specific photoinitiator comprising:
attaching one or more antennae to an α-amine enol ether compound having the following structure:

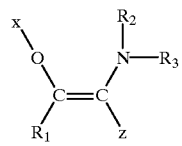

wherein $R_1$, $R_2$ and $R_3$ each independently represent H—, an alkyl group, a chalcone, phthaloylglycine, $HSO_3$—, $NaSO_3$—, vinyl thioether,

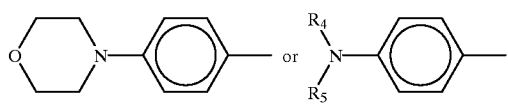

wherein $R_4$ and $R_5$ each independently represent an alkyl

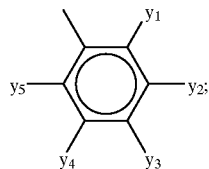

z group; x represents an alkyl group or represents an alkyl group, an alkylaryl group or

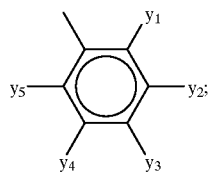

wherein $y_1$, $y_2$, $y_3$, $y_4$ and $y_5$ each independently represent H—, $HSO_3$—, $NaSO_3$—, HOOC—, NaOOC— and an alkyl group.

19. The method of claim 13, wherein the antennae comprise a chalcone, phthaloylglycine,

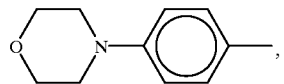

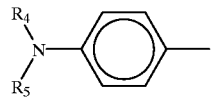

wherein $R_4$ and $R_5$ each independently represent an alkyl group, or

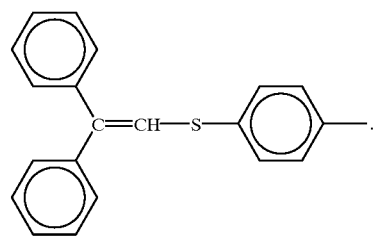

* * * * *